(12) United States Patent
Champagne et al.

(10) Patent No.: US 9,365,626 B2
(45) Date of Patent: Jun. 14, 2016

(54) SIMUKUNIN

(75) Inventors: Donald E. Champagne, Athens, GA (US); Hitoshi Tsujimoto, Bellefonte, PA (US); Ivo Francischetti, Bethesda, MD (US); Michael R. Strand, Athens, GA (US); Michail Kotsyfakis, Ceske Budejovice (CZ)

(73) Assignees: University of Georgia Research Foundation, Inc., Athens, GA (US); The United States of America, as represented by the Secretary of the Dept. of Health & Human Services, Washington, DC (US); Biology Centre CAS, v.v.i. (CZ)

(*) Notice: Subject to any disclaimer, the term of this patent is extended or adjusted under 35 U.S.C. 154(b) by 0 days.

(21) Appl. No.: 14/122,300

(22) PCT Filed: May 25, 2012

(86) PCT No.: PCT/US2012/039585
§ 371 (c)(1),
(2), (4) Date: Aug. 25, 2014

(87) PCT Pub. No.: WO2012/162611
PCT Pub. Date: Nov. 29, 2012

(65) Prior Publication Data
US 2015/0038419 A1 Feb. 5, 2015

Related U.S. Application Data

(60) Provisional application No. 61/490,149, filed on May 26, 2011.

(51) Int. Cl.
*C07K 14/435* (2006.01)
*C07K 14/745* (2006.01)
*A61K 38/17* (2006.01)

(52) U.S. Cl.
CPC ............ *C07K 14/435* (2013.01); *A61K 38/1709* (2013.01); *C07K 14/43577* (2013.01); *C07K 14/745* (2013.01)

(58) Field of Classification Search
CPC .................................................. C07K 14/435
See application file for complete search history.

(56) References Cited

U.S. PATENT DOCUMENTS

| | | | |
|---|---|---|---|
| 7,432,238 B2 | 10/2008 | Kisiel et al. | |
| 2005/0107301 A1 | 5/2005 | Cupp et al. | |
| 2010/0278752 A1 | 11/2010 | Kotsyfakis et al. | |
| 2011/0092413 A1 | 4/2011 | Hauser et al. | |

FOREIGN PATENT DOCUMENTS

| | | |
|---|---|---|
| WO | WO 2006/032436 A2 | 3/2006 |
| WO | WO 2012/162611 A1 | 11/2012 |

OTHER PUBLICATIONS

Andersen et al., 2009, An Insight into the Sialome of the Black Fly, *Simulium vittatum*, J Proteome Res, 8(3): 1474-1488.*
International Patent Application No. PCT/US2012/039585, filed May 25, 2012; International Search Report / Written Opinion issued Aug. 31, 2012 by U.S. ISA; 11 pages.
International Patent Application No. PCT/US2012/039585, filed May 25, 2012; International Preliminary Report on Patentability issued Dec. 5, 2013 by Switzerland IB of WIPO; 8 pages.
Abebe et al., "Anticoagulant activity in salivary gland extracts of black flies (Diptera: Simuliidae)," Nov. 1994, *J Med Entomol*; 31:908-911.
Abebe et al., "Simulidin: a black fly (*Simulium vittatum*) salivary gland protein with anti-thrombin activity," Nov. 1995, *J Insect Physiol*; 41:1001-1006.
Abebe et al., "Novel anticoagulant from salivary glands of Simulium vittatum (Diptera: Simuliidae) inhibits activity of coagulation factor V," Jan. 1996, *J Med Entomol*; 33:173-176.
Adam et al. "Inhibition of neutrophil elastase by the a1-proteinase inhibitor-immunoglobulin a complex". 1996. FEBS Letters. 385:201-204.
Albrecht et al., "Kunitz-type proteinase inhibitors derived by limited proteolysis of the inter-alpha-trypsin inhibitor, IX. Isolation and characterization of the inhibitory parts of inter-alpha-trypsin inhibitors from several mammalian sera," Dec. 1983, *Hoppe Seylers Z Physiol Chem*; 364:1697-1702.
Albrecht et al., "Elastase inhibition by the inter-alpha-trypsin inhibitor and derived inhibitors of man and cattle," Dec. 1983, *Hoppe Seylers Z Physiol Chem*; 364:1703-1708.
Andersen et al., "Insight into the sialome of the Black Fly, *Simulium vittatum*," Mar. 2009, *J Proteome Res*; 8(3):1474-1488.
Ascenzi et al., "The bovine basic pancreatic trypsin inhibitor (Kunitz inhibitor): a milestone protein," Jun. 2003, *Curr Protein Pept Sci*; 4:231-251.
Bernardo and Cupp, "Rearing black flies (Diptera: Simuliidae) in the laboratory: mass-scale in vitro membrane feeding and its application to collection of saliva and to parasitological and repellent studies," Dec. 1986, *J Med Entomol*; 23:666-679.

(Continued)

*Primary Examiner* — Amber D Steele
(74) *Attorney, Agent, or Firm* — Mueting, Raasch & Gebhardt, P.A.

(57) ABSTRACT

The present invention includes a novel protein, also referred to herein as simukunin, that inhibits the function of several physiologically important enzymes. Simukunin is a potent inhibitor of the blood coagulation cascade, inhibiting Factor Xa and functioning as an efficient anticoagulant. Simukunin also inhibits the serine proteases elastase and cathepsin and demonstrates anti-inflammatory properties. Also included are methods of making and using simukunin.

20 Claims, 7 Drawing Sheets

(56) References Cited

OTHER PUBLICATIONS

Calvo et al. "Alboserpin, a Factor Xa Inhibitor from the Mosquito Vector of Yellow Fever, Binds Heparin and Membrane Phospholipids and Exhibits Antithrombotic Activity" 2011. *The Journal of Biological Chemistry*. 286(32):27998-28010.

Chagas et al. "Anticoagulant activity in salivary gland homogenates of *Thyrosopelma guianense* (Diptera: Simuliidae), the primary vector of onchocerciasis in the Brazilian Amazon". 2010. Mem Inst Oswaldo Cruz, Rio de Janeiro. 105(1):174-178.

Champagne, "Antihemostatic strategies of blood-feeding arthropods," Dec. 2004, *Curr Drug Targets Cardiovasc Haematol Disord*; 4(4):375-96.

Champagne, "Antihemostatic molecules from saliva of blood-feeding arthropods," 2005, *Pathophysiol Haemost Thromb*; 34(4-5):221-7.

Cheng and Prusoff, "Relationship between the inhibition constant (K1) and the concentration of inhibitor which causes 50 per cent inhibition (I50) of an enzymatic reaction," Dec. 1973, *Biochem Pharmacol*; 22:3099-3108.

Chmelar et al., "A tick salivary protein targets cathepsin G and chymase and inhibits host inflammation and platelet aggregation," Jan. 13, 2011, *Blood*; 117:736-744. Available online on Oct. 12, 2010.

Corral-Rodriguez et al., "Tick-derived Kunitz-type inhibitors as antihemostatic factors," Sep. 2009, *Insect Biochem Mol Biol*; 39:579-595. Available online Jul. 24, 2009.

Crawley and Lane, "The haemostatic role of tissue factor pathway inhibitor," Feb. 2008, *Arterioscler Thromb Vasc Biol*; 28:233-242. Available online on Oct. 19, 2007.

Cupp et al., "Vasodilative activity in black fly salivary glands," Feb. 1994, *Am J Trop Med Hyg*; 50:241-246.

Cupp et al., "Analyses of cDNA and recombinant protein for a potent vasoactive protein in saliva of a blood-feeding black fly, *Simulium vittatum*," May 1998, *J Exp Biol*; 201:1553-1561.

Emanuelsson et al., "Locating proteins in the cell using TargetP, SignalP and related tools," 2007, *Nat Protoc*; 2:953-971.

Francischetti et al., "Ixolaris, a novel recombinant tissue factor pathway inhibitor (TFPI) from the salivary gland of the tick, *Ixodes scapularis*: identification of factor X and factor Xa as scaffolds for the inhibition of factor VIIa/tissue factor complex," May 2002, *Blood*; 99:3602-3612.

Francischetti et al., "Penthalaris, a novel recombinant five-Kunitz tissue factor pathway inhibitor (TFPI) from the salivary gland of the tick vector of Lyme disease, Ixodes scapularis," May 2004, *Thromb Haemost*; 91:886-898.

Francischetti et al., "The role of saliva in tick feeding," Jan. 1, 2009, *Front Biosci*; 14:2051-2088.

Fries and Blom, "Bikunin—not just a plasma proteinase inhibitor," Feb. 2000, *Int J Biochem Cell Biol*; 32:125-137.

Gray et al., "Laboratory Rearing of Black Flies," In: Maramorosch and Mahmood (Editors), *Maintenance of Human, Animal and Plant Pathogen Vectors*. New Delhi and Calcutta: Oxford & IBH Publishing Co. PVT. LTD; 1999.

Harvey, "Twenty years of dendrotoxins," Jan. 2001, *Toxicon*; 39:15-26.

Hector et al. Research Article. "In Vitro Inhibition of Neutrophil Elastase Activity by Inhaled Anti-Pseudomonas Antibiotics Used in Cystic Fibrosis Patients". 2010. Mediators of Inflammation. vol. 2010, Article ID 809591. 5 pages.

Jacobs et al., "Isolation and characterization of a coagulation factor Xa inhibitor from black fly salivary glands," Oct. 1990, *Thromb Haemost*; 64:235-238.

Julenius et al., "Prediction, conservation analysis, and structural characterization of mammalian mucin-type O-glycosylation sites," Feb. 2005, *Glycobiology*; 15:153-164. Available online on Sep. 22, 2004.

Kotsyfakis et al., "Selective cysteine protease inhibition contributes to blood-feeding success of the tick *Ixodes scapularis*," Oct. 5, 2007, *J Biol Chem*; 282:29256-29263. Available online on Aug. 13, 2007.

Kotsyfakis et al., "Antiinflammatory and Immunosuppressive Activity of Sialostatin L, a Salivary Cystatin from the Tick *Ixodes scapularis*". 2006. The Journal of Biological Chemistry. 281(36):26298-26307.

Kudo et al. "Research Article. Cathepsin G, a Neutrophil Protease, Induces Compact Cell-Cell Adhesion in MCF-7 Human Breast Cancer Cells". 2009. Mediators of Inflammation. vol. 2009. Article ID 850940. 11 pages.

Kuraki et al., "A novel oral neutrophil elastase inhibitor (ONO-6818) inhibits human neutrophil elastase-induced emphysema in rats," Aug. 15, 2002, *Am J Respir Crit Care Med*; 166(4):496-500.

Lai et al., "A thrombin inhibitor from the ixodid tick, *Amblyomma hebraeum*," Nov. 2004, *Gene*; 342:243-249.

Larkin et al., "Clustal W and Clustal X version 2.0," Nov. 1, 2007, *Bioinformatics*; 23:2947-2948. Available online on Sep. 10, 2007.

Levi and van der Poll, "Inflammation and coagulation," Feb. 2010, *Crit Care Med*; 38:S26-34.

Li et al., "Inhibition of arterial thrombus formation by ApoA1 Milano," Feb. 1999, *Arterioscler Thromb Vasc Biol*; 19:378-383.

Liener, "Trypsin inhibitors: concern for human nutrition or not?" May 1986, *J Nutr*; 116:920-923.

Macedo-Ribeiro et al., "Isolation, cloning and structural characterisation of boophilin, a multifunctional Kunitz-type proteinase inhibitor from the cattle tick," Feb. 20, 2008, *PLoS One*; 3:e1624; 17 pages.

Maritz-Olivier et al., "Tick anti-hemostatics: targets for future vaccines and therapeutics," Sep. 2007, *Trends Parasitol*; 23:397-407. Available online on Jul. 26, 2007.

McDougall et al., "Triggering of proteinase-activated receptor 4 leads to joint pain and inflammation in mice," Mar. 2009, *Arthritis Rheum*; 60:728-737.

Monteiro et al., "Ixolaris binding to factor X reveals a precursor state of factor Xa heparin-binding exosite," Jan. 2008, *Protein Sci*; 17:146-153. Available online on Nov. 27, 2007.

Morton et al., "Interpreting complex binding kinetics from optical biosensors: a comparison of analysis by linearization, the integrated rate equation, and numerical integration," May 1995, *Anal Biochem*; 227:176-185.

Nienaber et al., "Savignin, a potent thrombin inhibitor isolated from the salivary glands of the tick *Ornithodoros savignyi* (Acari: Argasidae)," Oct. 1999, *Exp Parasitol*; 93:82-91.

Oliveira et al., "Immunity to distinct sand fly salivary proteins primes the anti-Leishmania immune response towards protection or exacerbation of disease," Apr. 16, 2008, *PLoS Negl Trop Dis*; 2:e226.

Pagano et al. "Critical role of dipeptidyl peptidase I in neutrophil recruitment during the development of experimental abdominal aortic aneurysms". 2007. PNAS. 104(8):2855-2860.

Pham, "Neutrophil serine proteases: specific regulators of inflammation," Jul. 2006, *Nat Rev Immunol*; 6(7):541-50.

Pham, "Neutrophil serine proteases fine-tune the inflammatory response," 2008, *Int J Biochem Cell Biol*; 40:1317-1333. Available online on Nov. 29, 2007.

Raptis et al., "Serine protease cathepsin G regulates adhesion-dependent neutrophil effector functions by modulating integrin clustering," Jun. 2005, *Immunity*; 22(6):679-691.

Ribeiro and Francischetti, "Role of arthropod saliva in blood feeding: sialome and post-sialome perspectives," 2003, *Annu Rev Entomol*; 48:73-88. Available online on Jun. 4, 2002.

Ribeiro et al., "An insight into the sialotranscriptome of *Simulium nigrimanum*, a black fly associated with fogo selvagem in South America," Jun. 2010, *Am J Trop Med Hyg*; 82:1060-1075.

Salat et al. "Crystal structure and functional characterization of an immunomodulatory salivary cystatin from the soft tick *Ornithodoros moubata*". 2010. Biochem. J. pp. 103-112.

Saldeen et al., "Differential effects of alpha- and gamma-tocopherol on low-density lipoprotein oxidation, superoxide activity, platelet aggregation and arterial thrombogenesis," Oct. 1999, *J Am Coll Cardiol*; 34:1208-1215.

Schneider and Higgs, "The enhancement of arbovirus transmission and disease by mosquito saliva is associated with modulation of the host immune response," May 2008, *Trans R Soc Trop Med Hyg*; 102:400-408. Available online on Mar. 14, 2008.

(56) References Cited

OTHER PUBLICATIONS

Tatusova et al., "BLAST 2 Sequences, a new tool for comparing protein and nucleotide sequences," May 1999 *FEMS Microbiol Lett*, 174:247-250.
Titus and Ribeiro, "Salivary gland lysates from the sand fly *Lutzomyia longipalpis* enhance Leishmania infectivity," Mar. 1988, *Science*; 239:1306-1308.
Trivedi and Caughey, "Mast cell peptidases: chameleons of innate immunity and host defense," Mar. 2010, *Am J Respir Cell Mol Biol*; 42:257-267. Available online on Nov. 20, 2009.
Tschesche and Wenzel, "Peptide/protein inhibitors of trypsin and kallikrein—primary structural requirements," 1983, *Adv Exp Med Biol*; 156:329-337.
Tschesche et al., "Semisynthetic engineering of proteinase inhibitor homologues," May 1987, *Biochim Biophys Acta*; 913:97-101.
Tsujimoto et al., "Black fly salivary gland extract inhibits proliferation and induces apoptosis in murine splenocytes," Apr. 2010, *Parasite Immunol*; 32(4):275-84.
Tsujimoto et al., "Simukunin from the Salivary Glands of the Black Fly *Simulium vittatum* Inhibits Enzymes That Regulate Clotting and Inflammatory Responses," Feb. 2012, *PLoS One*; 7(2):e29964; 11 pages.
UniProt Accession No. B5M0W4_SIMVI [online]. Protein: Single Kunitz protease inhibitor; Organism: *Simulium vittatum* (Striped black fly). UniProt Consortium: European Bioinformatics Institute (EMBL-EBI; Cambridge, United Kingdom), SIB Swiss Institute of Bioinformatics (Geneva, Switzerland), and Protein Information Resource (PIR; Washington, DC, United States of America) [retrieved on Apr. 28, 2015]. Retrieved from the Internet: <http://www.uniprot.org/uniprot/B5M0W4>; 4 pgs.
Valenzuela et al., "A novel inhibitor of factor X activation from the salivary glands of the bed bug *Cimex lectularius*," Jul. 1996, *Exp Parasitol*; 83:184-190.
van de Locht et al., "The ornithodorin-thrombin crystal structure, a key to the TAP enigma?" Nov. 1996, *EMBO J*; 15:6011-6017.
Vincent and Lazdunski, "The interaction between alpha-chymotrypsin and pancreatic trypsin inhibitor (Kunitz inhibitor). Kinetic and thermodynamic properties," Oct. 1973, *Eur J Biochem*; 38:365-372.
Wanasen et al., "Differential modulation of murine host immune response by salivary gland extracts from the mosquitoes *Aedes aegypti* and *Culex quinquefasciatus*," Jun. 2004, *Med Vet Entomol*; 18(2):191-9.
Wasserman et al., "Saliva of the Yellow Fever mosquito, *Aedes aegypti*, modulates murine lymphocyte function," Jun.-Jul. 2004, *Parasite Immunol*; 26(6-7):295-306.
Zancan and Mourao, "Venous and arterial thrombosis in rat models: dissociation of the antithrombotic effects of glycosaminoglycans," Jan. 2004, *Blood Coagul Fibrinolysis*; 15(1): 45-54.
Zhao et al., "Cytokine production by skin-derived mast cells: endogenous proteases are responsible for degradation of cytokines," Aug. 2005, *J Immunol*; 175:2635-2642.
Caljon et al., "Identification of a Tsetse Fly Salivary Protein with Dual Inhibitory Action on Human Platelet Aggregation," Mar 2010, *PLOS One*;5(3):12 pgs.
Calvo et al., "Aegyptin, a Novel Mosquito Salivary Gland Protein, Specifically Binds to Collagen and Prevents Its Interaction with Platelet Glycoprotein VI, Integrin α2β1, and von Willebrand Factor" Sep. 2007, *The Journal of Biological Chemistry*, 282(37): 26928-26938.
Chand et al., Structure-Function Analysis of the Reactive Site in the First Kunitz-type Domain of Human Tissue Factor Pathway Inhibitor-2, Apr 2004; *The Journal of Biological Chemistry*, 279(17):17500-17507.
National Center for Biotechnology Information, National Library of Medicine, National Institutes of Health, GenBank Locus AAI49369, Accession No. AAI49369, "PTI protein [*Bos taurus*]," [online]. Bethesda, MD [retrieved on Aug. 5, 2015]. Retrieved from the Internet at: ncbi.nlm.nih.gov/protein/AAI49369.1?report=genpept&log$=seqview; 2 pgs.
National Center for Biotechnology Information, National Library of Medicine, National Institutes of Health, GenBank Locus AAR97367, Accession No. AAR97367, "thrombin inhibitor [*Amblyomma hebraeum*]," [online]. Bethesda, MD [retrieved on Aug. 5, 2015]. Retrieved from the Internet at: ncbi.nlm.nih.gov/protein/AAR97367; 2 pgs.
National Center for Biotechnology Information, National Library of Medicine, National Institutes of Health, GenBank Locus AY083375, Accession No. AY083375, "*Simulium vittatum* actin mRNA, partial cds.," [online]. Bethesda, MD [retrieved on Aug. 5, 2015]. Retrieved from the Internet at: ncbi.nlm.nih.gov/nuccore/AY083375.1; 2 pgs.
National Center for Biotechnology Information, National Library of Medicine, National Institutes of Health, GenBank Locus CAC82583, Accession No. CAC82583, "boophilin [*Rhipicephalus microplus*]," [online]. Bethesda, MD [retrieved on Aug. 5, 2015]. Retrieved from the Internet at: ncbi.nlm.nih.gov/protein/CAC82583; 2 pgs.
National Center for Biotechnology Information, National Library of Medicine, National Institutes of Health, GenBank Locus EU930227, Accession No. EU930227, "*Simulium vittatum* clone SV-170 single Kunitz protease inhibitor mRNA, complete cds.," [online]. Bethesda, MD [retrieved on Aug. 5 2015 ]. Retrieved from the Internet at: ncbi.nlm.nih.gov/nuccore/EU930227; 1 pg.
National Center for Biotechnology Information, National Library of Medicine, National Institutes of Health, GenBank Locus EU930300, Accession No. EU930300, "*Simulium vittatum* clone SV-66 single Kunitz protease inhibitor mRNA, complete cds.," [online]. Bethesda, MD [retrieved on Aug. 5, 2015]. Retrieved from the Internet at: ncbi.nlm.nih.gov/nuccore/EU9303000; 1 pg.
National Center for Biotechnology Information, National Library of Medicine, National Institutes of Health, GenBank Locus TFPI1_HUMAN, Accession No. P10646, "RecName: Full=Tissue factor pathway inhibitor; Short=TFPI; AltName: Full=Extrinsic pathway inhibitor; Short=EPI; AltName: Full=Lipoprotein-associated coagulation inhibitor; Short=LACI; Flags: Precursor," [online]. Bethesda, MD [retrieved on Aug. 5, 2015]. Retrieved from the Internet at: ncbi.nlm.nih.gov/protein/P10646; 1 pg.

\* cited by examiner

```
TGAATTGGATCGAAATGAATATACTTCCAATAAGTGCTTTCTTCCTGCTATATCTTGGCCATTCTTTGGCCCAA
          M  N  I  L  P  I  S  A  F  F  L  L  Y  L  G  H  S  L  A  Q
         -19                          -10                             1

GAGAACGTTTGCAATCTTCCGGTGGACGAAGGTGTATGTAGAGCGTTATTCAAGCGTTTTTACTACGAACCCGCA
 E  N  V  C  N  L  P  V  D  E  G  V  C  R  A  L  F  K  R  F  Y  Y  E  P  A
                        10                      20

ACCGATAGTTGCAAAGAGTTCTACTATGGAGGTTGTGAGGGAAATGGGAACAGGTTCAAAAGTAAAAAGGAATGC
 T  D  S  C  K  E  F  Y  Y  G  G  C  E  G  N  G  N  R  F  K  S  K  K  E  C
          30                      40                                  50

ATTCTCAAGTGTCAGAAGAATAAACAGCTCATAAAAACAAGAAAACGCAAACCAAAAAAGACAACCAAACCCCCG
 I  L  K  C  Q  K  N  K  Q  L  I  K  T  R  K  R  K  P  K  K  T  T  K  P  P
                        60                      70

ATACCAATTATTTCGTTGGACTAAAAAGGACATTCAAACTAAGTTATAGACAAACATTTATATTTCACAATTACT
 I  P  I  I  S  L  D  -
                   80

TGAAAAATAAAATCGAACTGTGAAAAATTTTAATTTGACCAGAAAAAAAAAAAAAAAAAAAAAA
```

SV-170

```
GCATTAATCATTAGTACACCTGAGAGAATCTTCTGCGTCAAAGTATGTGAAAACAATCATCCTCGGAACAATC
                                         M  L  K  T  I  I  L  G  T  I
                                        -22

GCCATACTGATATGTATGGCAAACAATTCTGAAGCAAAGTCAGCTGACATCTGCAGACTTCCAATGGATAAAGGT
 A  I  L  I  C  M  A  N  N  S  E  A  K  S  A  D  I  C  R  L  P  M  D  K  G
         -10                         1                              10

ATTTGCACTCCAACAGAATGGCGTTATCATTTTGACCCAGCGAAAAACAAGTGCTTTATGTTTCCGTGGGGATGC
 I  C  T  P  T  E  W  R  Y  H  F  D  P  A  K  N  C  F  M  F  P  W  G  C
            20                              30

CTTGGGAATGCGAACAATTTCAAAACCAGACAAGAATGTAAAGCCAAGTGTATGTAACAAGACAGCACAAGAGGA
 L  G  N  A  N  N  F  K  T  R  Q  E  C  K  A  K  C  M  -
       40                      50

TAAAAATGTATTGACCGATTGTTATTAAAATAAGGCATAAACAATTTGATAGACAAAACTGAAAAAAAAAAAAAA
AAAAAA
```

*Figure 1B*

| | | | | | | | |
|---|---|---|---|---|---|---|---|
| SV66 | 1 | --QENV---- | NLPVDEGV | LFKREYYEPATDS | KEFYYGG | EGNGRFKSKKE | ILKQKNK 59 |
| TFPI_KU1 | 22 | --MHSF---- | AFKADDGP | TMKRFFFNIFTRQ | EEFYYGG | EGNQRFESLEE | KRMTRD- 79 |
| TFPI_KU2 | 93 | --KPDF---- | FLEEDPGI | YITRYFYNNQTKQ | EREFKYGG | LGNMNNFETLEE | RNIEDGP 151 |
| TFPI_KU3 | 185 | --GPSW---- | LTPADRGL | NENRFINSVIGK | RPFKYSG | GGNEMNFTSKQE | LRAKKGF 243 |
| BPTI | 1 | --RPDF---- | LEPPYTGP | RMIRYFYNAKAGL | QPFVYGG | RAKRNNFKSSED | MRTGGA- 59 |
| Amblin_KU1 | 1 | QRVPGY---- | KKKPAVGP | LIEKWIFDYSTQS | KTFYIGG | GGNGKFSSRKK | REALPKR 61 |
| Amblin_KU2 | 62 | -PSVPV---- | KQMPDPGF | YMPHWTFNSKSGY | EGFVYGG | QGNDRFKSCWQ | MKKRTAR 121 |
| Boophilin_KU1 | 1 | -QRNGF---- | RLPADEGI | LIPRFYFNTETGK | TMFSYGG | GGNEMNFETIEE | QKAGAPE 60 |
| Boophilin_KU2 | 66 | -ESADFKTG | EPAADSGS | AGQLERWFNVQSGE | ETFVYGG | GGNDNYESEEE | EIVKNM- 127 |
| SV170 | 1 | -KSADI---- | RLPMDKGI | TPTEWRYHFDPAKNK | FMFPWG- | LGNANNFKTRQE | KAKM--- 56 |

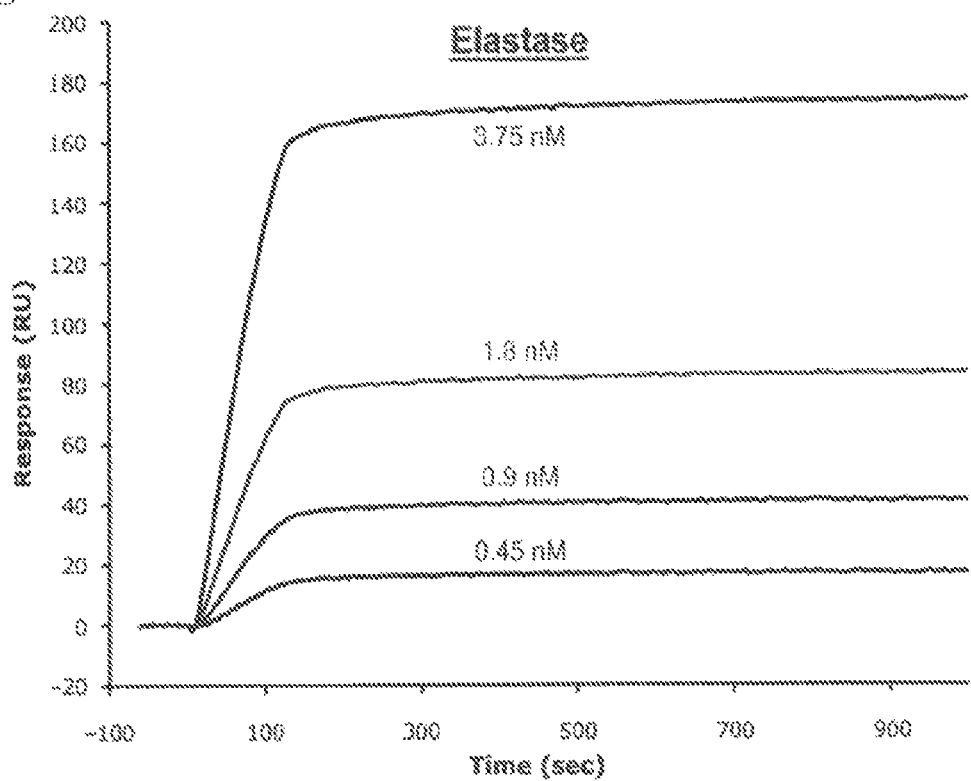

```
SEQUENCE LISTING

<160> NUMBER OF SEQ ID NOS: 36

<210> SEQ ID NO 1
<211> LENGTH: 430
<212> TYPE: DNA
<213> ORGANISM: Simulium vittatum

<400> SEQUENCE: 1
tgaattggat cgaaatgaat atacttccaa taagtgcttt cttcctgcta tatcttggcc     60
attctttggc ccaagagaac gtttgcaatc ttccggtgga cgaaggtgta tgtagagcgt    120
tattcaagcg tttttactac gaacccgcaa ccgatagttg caaagagttc tactatggag    180
gttgtgaggg aaatgggaac aggttcaaaa gtaaaaagga atgcattctc aagtgtcaga    240
agaataaaca gctcataaaa acaagaaaac gcaaaccaaa aaagacaacc aaaccccga     300 taccaattat ttcgttggac taaaaaggac attcaaacta agttatagac aaacatttat    360
atttcacaat tacttgaaaa ataaaatcga actgtgaaaa attttaattt gaccagaaaa    420
aaaaaaaaaa                                                          430

<210> SEQ ID NO 2
<211> LENGTH: 102
<212> TYPE: PRT
<213> ORGANISM: Simulium vittatum

<400> SEQUENCE: 2

Met Asn Ile Leu Pro Ile Ser Ala Phe Phe Leu Leu Tyr Leu Gly His
1               5                   10                  15

Ser Leu Ala Gln Glu Asn Val Cys Asn Leu Pro Val Asp Glu Gly Val
```

```
            20                  25                  30

Cys Arg Ala Leu Phe Lys Arg Phe Tyr Tyr Glu Pro Ala Thr Asp Ser
            35                  40                  45

Cys Lys Glu Phe Tyr Tyr Gly Gly Cys Glu Gly Asn Gly Asn Arg Phe
        50                  55                  60

Lys Ser Lys Lys Glu Cys Ile Leu Lys Cys Gln Lys Asn Lys Gln Leu
65                  70                  75                  80

Ile Lys Thr Arg Lys Arg Lys Pro Lys Lys Thr Thr Lys Pro Pro Ile
                85                  90                  95

Pro Ile Ile Ser Leu Asp
            100

<210> SEQ ID NO 3
<211> LENGTH: 83
<212> TYPE: PRT
<213> ORGANISM: Simulium vittatum

<400> SEQUENCE: 3

Gln Gl

```
                    35                  40                  45
Ala Lys Asn Lys Cys Phe Met Phe Pro Trp Gly Cys Leu Gly Asn Ala
 50                  55                  60

Asn Asn Phe Lys Thr Arg Gln Glu Cys Lys Ala Lys Cys Met
 65                  70                  75
```

<210> SEQ ID NO 6
<211> LENGTH: 56
<212> TYPE: PRT
<213> ORGANISM: Simulium vittatum

<400> SEQUENCE: 6

```
Lys Ser Ala Asp Ile Cys Arg Leu Pro Met Asp Lys Gly Ile Cys Thr
 1               5                  10                  15

Pro Thr Glu Trp Arg Tyr His Phe Asp Pro Ala Lys Asn Lys Cys Phe
                20                  25                  30

Met Phe Pro Trp Gly Cys Leu Gly Asn Ala Asn Asn Phe Lys Thr Arg
            35                  40                  45

Gln Glu Cys Lys Ala Lys Cys Met
 50                  55
```

<210> SEQ ID NO 7
<211> LENGTH: 59
<212> TYPE: PRT
<213> ORGANISM: Simulium vittatum

<400> SEQUENCE: 7

```

```
Ile Met Lys Arg Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
    50                  55
```

<210> SEQ ID NO 10
<211> LENGTH: 59
<212> TYPE: PRT
<213> ORGANISM: Homo sapiens

<400> SEQUENCE: 10

```
Lys Pro Asp Phe Cys Phe Leu Glu Glu Asp Pro Gly Ile Cys Arg Gly
1               5                   10                  15

Tyr Ile Thr Arg Tyr Phe Tyr Asn Asn Gln Thr Lys Gln Cys Glu Arg
            20                  25                  30

Phe Lys Tyr Gly Gly Cys Leu Gly Asn Met Asn Asn Phe Glu Thr Leu
            35                  40                  45

Glu Glu Cys Lys Asn Ile Cys Glu Asp Gly Pro
    50                  55
```

<210> SEQ ID NO 11
<211> LENGTH: 59
<212> TYPE: PRT
<213> ORGANISM: Homo sapiens

<400> SEQUENCE: 11

```
Gly Pro Ser Trp Cys Leu Thr Pro Ala Asp Arg Gly Leu Cys Arg Ala
1               5                   10                  15

Asn Glu Asn Arg Phe Tyr Tyr Asn Ser Val Ile Gly Lys Cys Arg Pro
            20                  25                  30

Phe Lys Tyr Ser Gly Cys Gly Gly Asn Glu Asn Asn Phe Thr Ser Lys
            35                  40                  45

Gln Glu Cys Leu Arg Ala Cys Lys Lys Gly Phe
    50                  55
```

<210> SEQ ID NO 12
<211> LENGTH: 58
<212> TYPE: PRT
<213> ORGANISM: Bos taurus

<400> SEQUENCE: 12

```
Arg Pro Asp Phe Cys Leu Glu Pro Pro Tyr Thr Gly Pro Cys Lys Ala
1               5                   10                  15

Arg Met Ile Arg Tyr Phe Tyr Asn Ala Lys Ala Gly Leu Cys Gln Pro
            20                  25                  30

Phe Val Tyr Gly Gly Cys Arg Ala Lys Arg Asn Asn Phe Lys Ser Ser
            35                  40                  45

Glu Asp Cys Met Arg Thr Cys Gly Gly Ala
    50                  55
```

<210> SEQ ID NO 13
<211> LENGTH: 61
<212> TYPE: PRT
<213> ORGANISM: Amblyomma hebraeum

<400> SEQUENCE: 13

```
Gln Arg Val Pro Gly Tyr Cys Lys Lys Pro Ala Val Gly Pro Cys
1               5                   10                  15
```

```
Lys Ala Leu Ile Glu Lys Trp Tyr Phe Asp Tyr Ser Thr Gln Ser Cys
            20                  25                  30

Lys Thr Phe Tyr Tyr Gly Gly Cys Gly Gly Asn Gly Asn Lys Phe Ser
            35                  40                  45

Ser Arg Lys Lys Cys Arg Glu Ala Cys Leu Pro Lys Arg
 50                  55                  60

<210> SEQ ID NO 14
<211> LENGTH: 60
<212> TYPE: PRT
<213> ORGANISM: Amblyomma hebraeum

<400> SEQUENCE: 14

Pro Ser Val Pro Val Cys Lys Gln Met Pro Asp Pro Gly Phe Cys Arg
1               5                   10                  15

Ala Tyr Met Pro His Trp Phe Phe Asn Ser Lys Ser Gly Tyr Cys Glu
            20                  25                  30

Gly Phe Val Tyr Gly Gly Cys Gln Gly Asn Asp Asn Arg Phe Lys Ser
            35                  40                  45

Cys Trp Gln Cys Met Lys Lys Cys Arg Thr Ala Arg
 50                  55                  60

<210> SEQ ID NO 15
<211> LENGTH: 60
<212> TYPE: PRT
<213> ORGANISM: Rhipicephalus microplus

<400> SEQUENCE: 15

Gln Arg Asn Gly Phe Arg Arg Leu Pro Ala Asp Glu Gly Ile Cys Lys
1               5                   10                  15

Ala Leu Ile Pro Arg Phe Tyr Phe Asn Thr Glu Thr Gly Lys Cys Thr
            20                  25                  30

Met Phe Ser Tyr Gly Gly Cys Gly Gly Asn Glu Asn Asn Phe Glu Thr
            35                  40                  45

Ile Glu Glu Cys Gln Lys Ala Cys Gly Ala Pro Glu
 50                  55                  60

<210> SEQ ID NO 16
<211> LENGTH: 62
<212> TYPE: PRT
<213> ORGANISM: Rhipicephalus microplus

<400> SEQUENCE: 16

Glu Ser Ala Asp Phe Lys Thr Gly Cys Glu Pro Ala Ala Asp Ser Gly
1               5                   10                  15

Ser Cys Ala Gly Gln Leu Glu Arg Trp Phe Tyr Asn Val Gln Ser Gly
            20                  25                  30

Glu Cys Glu Thr Phe Val Tyr Gly Gly Cys Gly Gly Asn Asp Asn Asn
            35                  40                  45

Tyr Glu Ser Glu Glu Glu Cys Glu Leu Val Cys Lys Asn Met
 50                  55                  60

<210> SEQ ID NO 17
<211> LENGTH: 24
<212> TYPE: DNA
<213> ORGANISM: artificial
<220> FEATURE:
<223> OTHER INFORMATION: synthetic oligonucleotide primer

<400> SEQUENCE: 17
```

```
tgtgttacgt tgccttggac tttg                                          24
```

<210> SEQ ID NO 18
<211> LENGTH: 25
<212> TYPE: DNA
<213> ORGANISM: artificial
<220> FEATURE:
<223> OTHER INFORMATION: synthetic oligonucleotide primer

<400> SEQUENCE: 18

```
tgatggagtt gtagacggtt tcgtg                                         25
```

<210> SEQ ID NO 19
<211> LENGTH: 29
<212> TYPE: DNA
<213> ORGANISM: artificial
<220> FEATURE:
<223> OTHER INFORMATION: synthetic oligonucleotide primer

<400> SEQUENCE: 19

```
tgaattggat cgaaatgaat atacttcca                                     29
```

<210> SEQ ID NO 20
<211> LENGTH: 30
<212> TYPE: DNA
<213> ORGANISM: artificial
<220> FEATURE:
<223> OTHER INFORMATION: synthetic oligonucleotide primer

<400> SEQUENCE: 20

```
ttagtttgaa tgtccttttt agtccaacga                                    30
```

<210> SEQ ID NO 21
<211> LENGTH: 26
<212> TYPE: DNA
<213> ORGANISM: artificial
<220> FEATURE:
<223> OTHER INFORMATION: synthetic oligonucleotide primer

<400> SEQUENCE: 21

```
cacctgagag aatcttctgc gtcaaa                                        26
```

<210> SEQ ID NO 22
<211> LENGTH: 29
<212> TYPE: DNA
<213> ORGANISM: artificial
<220> FEATURE:
<223> OTHER INFORMATION: synthetic oligonucleotide primer

<400> SEQUENCE: 22

```
cggtcaatac atttttatcc tcttgtgct                                     29
```

<210> SEQ ID NO 23
<211> LENGTH: 37
<212> TYPE: DNA
<213> ORGANISM: artificial
<220> FEATURE:
<223> OTHER INFORMATION: synthetic oligonucleotide primer

<400> SEQUENCE: 23

```
gacgacgaca agatgcaaga gaacgtttgc aatcttc                            37
```

<210> SEQ ID NO 24
<211> LENGTH: 39
<212> TYPE: DNA

<213> ORGANISM: artificial
<220> FEATURE:
<223> OTHER INFORMATION: synthetic oligonucleotide primer

<400> SEQUENCE: 24
gaggagaagc ccggttagtc caacgaaata attggtatc                39

<210> SEQ ID NO 25
<211> LENGTH: 40
<212> TYPE: DNA
<213> ORGANISM: artificial
<220> FEATURE:
<223> OTHER INFORMATION: synthetic oligonucleotide primer

<400> SEQUENCE: 25
gaggagaagc ccggtgcgtc caacgaaata attggtatcg               40

<210> SEQ ID NO 26
<211> LENGTH: 36
<212> TYPE: DNA
<213> ORGANISM: artificial
<220> FEATURE:
<223> OTHER INFORMATION: synthetic oligonucleotide primer

<400> SEQUENCE: 26
gacgacgaca agatgaagtc agctgacatc tgcaga                   36

<210> SEQ ID NO 27
<211> LENGTH: 39
<212> TYPE: DNA
<213> ORGANISM: artificial
<220> FEATURE:
<223> OTHER INFORMATION: synthetic oligonucleotide primer

<400> SEQUENCE: 27
gaggagaagc ccggttacat acacttggct ttacattct                39

<210> SEQ ID NO 28
<211> LENGTH: 41
<212> TYPE: DNA
<213> ORGANISM: artificial
<220> FEATURE:
<223> OTHER INFORMATION: synthetic oligonucleotide primer

<400> SEQUENCE: 28
gaggagaagc ccggtgccat acacttggct ttacattctt g             41

<210> SEQ ID NO 29
<211> LENGTH: 33
<212> TYPE: DNA
<213> ORGANISM: artificial
<220> FEATURE:
<223> OTHER INFORMATION: synthetic oligonucleotide primer

<400> SEQUENCE: 29
ccggtggacg aaggtgcatg tagagcgtta ttc                      33

<210> SEQ ID NO 30
<211> LENGTH: 33
<212> TYPE: DNA
<213> ORGANISM: artificial
<220> FEATURE:
<223> OTHER INFORMATION: synthetic oligonucleotide primer -continued

```
<400> SEQUENCE: 30
gaataacgct ctacatgcac cttcgtccac cgg                                    33

<210> SEQ ID NO 31
<211> LENGTH: 40
<212> TYPE: DNA
<213> ORGANISM: artificial
<220> FEATURE:
<223> OTHER INFORMATION: synthetic oligonucleotide primer

<400> SEQUENCE: 31
aatcttccgg tggacgaagg tgtagctaga gcgttattca                             40

<210> SEQ ID NO 32
<211> LENGTH: 40
<212> TYPE: DNA
<213> ORGANISM: artificial
<220> FEATURE:
<223> OTHER INFORMATION: synthetic oligonucleotide primer

<400> SEQUENCE: 32
tgaataacgc tctagctaca ccttcgtcca ccggaagatt                             40

<210> SEQ ID NO 33
<211> LENGTH: 40
<212> TYPE: DNA
<213> ORGANISM: artificial
<220> FEATURE:
<223> OTHER INFORMATION: synthetic oligonucleotide primer

<400> SEQUENCE: 33
cttccggtgg acgaaggtgt atgtgcagcg ttattcaagc                             40

<210> SEQ ID NO 34
<211> LENGTH: 40
<212> TYPE: DNA
<213> ORGANISM: artificial
<220> FEATURE:
<223> OTHER INFORMATION: synthetic oligonucleotide primer

<400> SEQUENCE: 34
gcttgaataa cgctgcacat acaccttcgt ccaccggaag                             40

<210> SEQ ID NO 35
<211> LENGTH: 42
<212> TYPE: DNA
<213> ORGANISM: artificial
<220> FEATURE:
<223> OTHER INFORMATION: synthetic oligonucleotide primer

<400> SEQUENCE: 35
ggtgtatgta gagcgttatt cgcgcgtttt tactacgaac cc                          42

<210> SEQ ID NO 36
<211> LENGTH: 42
<212> TYPE: DNA
<213> ORGANISM: artificial
<220> FEATURE:
<223> OTHER INFORMATION: synthetic oligonucleotide primer

<400> SEQUENCE: 36
gggttcgtag taaaaacgcg cgaataacgc tctacataca cc                          42
```

SIMUKUNIN

CONTINUING APPLICATION DATA

This application is the §371 U.S. National Stage of International Application No. PCT/US2012/039585, filed 25 May 2012, which claims the benefit of U.S. Provisional Application Ser. No. 61/490,149, filed May 26, 2011, each of which are incorporated by reference herein.

BACKGROUND

Certain medical conditions, such as strokes, cardiovascular blockages, deep vein thrombosis, and pulmonary embolism, are treated with the administration of an anticoagulant, to prevent the formation of blood clots and the extension of existing clots. A widely used anticoagulant is heparin. However, some patients develop allergic responses to heparin and a serious side-effect of heparin is heparin-induced thrombocytopenia (HIT). HIT is caused by an immunological reaction that makes platelets a target of immunological response, resulting in the degradation of platelets and causing thrombocytopenia. These patients would benefit from the availability of alternative anticoagulants.

Heparin results in the inactivation of thrombin and other proteases involved in blood clotting (most notably factor Xa). The actions of heparin are limited to anticoagulant activity and heparin does not demonstrate anti-inflammatory activity. Alternatives to heparin, possessing both anticoagulant activity and additional activities, such as anti-inflammatory activity, are needed. Such alternatives, demonstrating, for example, both anticoagulant and anti-inflammatory activities, could be administered in the early stages of a medical crisis to both antagonize clot formation and to limit tissue damage caused by inflammatory responses.

SUMMARY OF THE INVENTION

The present invention includes an isolated simukunin polypeptide having an amino acid sequence at least about 80% identical to SEQ ID NO:3 and fragments thereof, wherein the simukunin polypeptide inhibits Factor Xa. In some aspects, the isolated simukunin polypeptide also inhibits elastase and/or cathepsin G.

The present invention includes an isolated simukunin polypeptide having an amino acid sequence at least about 95% identical to SEQ ID NO:3 and fragments thereof, wherein the simukunin polypeptide inhibits Factor Xa. In some aspects, the isolated simukunin polypeptide also inhibits elastase and/or cathepsin G.

The present invention includes an isolated simukunin polypeptide having an amino acid sequence at least about 95% identical to SEQ ID NO:3 and fragments thereof, wherein the isolated simukunin polypeptide inhibits Factor Xa, inhibits elastase, and inhibits cathepsin G.

In some aspects, an isolated simukunin polypeptide of the present invention also inhibits Factor IXa, Factor XIa, plasmin, kallikrein, trypsin, and/or β-tryptase.

The present invention includes compositions of an isolated simukunin polypeptide as described herein. In some aspects, the composition includes a pharmaceutically acceptable carrier. In some aspects, the pharmaceutically acceptable carrier is pyrogen free. In some aspects, a composition is pyrogen free.

In some aspects, the present invention includes a composition including an isolated simukunin polypeptide having an amino acid sequence at least about 95% identical to SEQ ID NO:3 and fragments thereof, wherein the isolated simukunin polypeptide inhibits Factor Xa, inhibits elastase, and inhibits cathepsin G, wherein the composition is pyrogen free.

In some aspects, a composition of the present invention is formulated for parenteral application.

In some aspects, a composition of the present invention is formulated for topical application.

The present invention includes an isolated polynucleotide sequence encoding a simukunin polypeptide as described herein. In some aspects, the present invention includes a vector or host cell including an isolated polynucleotide sequence.

The present invention includes a method of producing a polypeptide, the method including culturing a host cell as described herein and purifying an expression product from the cell mass and/or the culture medium.

The present invention includes a method of inhibiting plasma coagulation, the method including providing an isolated simukunin polypeptide as described herein or a composition as described herein. In some aspects, the isolated polypeptide is provided in vitro. In some aspects, the isolated polypeptide is provided in vivo to a subject. In some aspect, administration is parenteral. In some aspects, administration is topical.

The present invention includes a method of inhibiting Factor Xa, the method including providing an isolated simukunin polypeptide as described herein or a composition as described herein. In some aspects, the isolated polypeptide is provided in vitro. In some aspects, the isolated polypeptide is provided in vivo to a subject. In some aspect, administration is parenteral. In some aspects, administration is topical.

The present invention includes a method of inhibiting one or more serine proteases, the method including providing an isolated simukunin polypeptide as described herein or a composition as described herein. In some aspects, the isolated polypeptide is provided in vitro. In some aspects, the isolated polypeptide is provided in vivo to a subject. In some aspect, administration is parenteral. In some aspects, administration is topical.

The present invention includes a method of inhibiting elastase and/or cathepsin G, the method including providing an isolated simukunin polypeptide as described herein or a composition as described herein. In some aspects, the isolated polypeptide is provided in vitro. In some aspects, the isolated polypeptide is provided in vivo to a subject. In some aspect, administration is parenteral. In some aspects, administration is topical.

The present invention includes a method of inhibiting Factor IXa, Factor XIa, and/or plasmin, the method including providing an isolated simukunin polypeptide as described herein or a composition as described herein. In some aspects, the isolated polypeptide is provided in vitro. In some aspects, the isolated polypeptide is provided in vivo to a subject. In some aspect, administration is parenteral. In some aspects, administration is topical.

The present invention includes a method of inhibiting kallikrein, trypsin, and/or β-tryptase, the method including providing an isolated simukunin polypeptide as described herein or a composition as described herein. In some aspects, the isolated polypeptide is provided in vitro. In some aspects, the isolated polypeptide is provided in vivo to a subject. In some aspect, administration is parenteral. In some aspects, administration is topical.

The present invention includes a method of modulating inflammation, the method including providing an isolated simukunin polypeptide as described herein or a composition as described herein. In some aspects, the isolated polypeptide is provided in vitro. In some aspects, the isolated polypeptide is provided in vivo to a subject. In some aspect, administration is parenteral. In some aspects, administration is topical.

The present invention includes a method of modulating the function of neutrophils, macrophages, and/or mast cells, the method including providing an isolated simukunin polypeptide as described herein or a composition as described herein. In some aspects, the isolated polypeptide is provided in vitro. In some aspects, the isolated polypeptide is provided in vivo to a subject. In some aspect, administration is parenteral. In some aspects, administration is topical.

The present invention includes a method of inhibiting plasma coagulation in a subject, the method including administering to the subject an isolated simukunin polypeptide as described herein or a composition as described herein. In some aspects, the isolated simukunin polypeptide includes an amino acid sequence at least about 95% identical to SEQ ID NO:3 and wherein the isolated simukunin polypeptide inhibits Factor Xa, elastase, and cathepsin G. In some aspect, administration is parenteral. In some aspects, administration is topical.

The present invention includes a method of inhibiting Factor Xa in a subject, the method including administering to the subject an isolated simukunin polypeptide as described herein or a composition as described herein. In some aspects, the isolated simukunin polypeptide includes an amino acid sequence at least about 95% identical to SEQ ID NO:3 and wherein the isolated simukunin polypeptide inhibits Factor Xa, elastase, and cathepsin G. In some aspect, administration is parenteral. In some aspects, administration is topical.

The present invention includes a method of inhibiting elastase and/or cathepsin G in a subject, the method including administering to the subject an isolated simukunin polypeptide as described herein or a composition as described herein. In some aspects, the isolated simukunin polypeptide includes an amino acid sequence at least about 95% identical to SEQ ID NO:3 and wherein the isolated simukunin polypeptide inhibits Factor Xa, elastase, and cathepsin G. In some aspect, administration is parenteral. In some aspects, administration is topical.

The present invention includes a method of inhibiting Factor Xa and elastase in a subject, the method including administering to the subject an isolated simukunin polypeptide as described herein or a composition as described herein. In some aspects, the isolated simukunin polypeptide includes an amino acid sequence at least about 95% identical to SEQ ID NO:3 and wherein the isolated simukunin polypeptide inhibits Factor Xa, elastase, and cathepsin G. In some aspect, administration is parenteral. In some aspects, administration is topical.

The present invention includes a method of modulating inflammation in a subject, the method including administering to the subject an isolated simukunin polypeptide as described herein or a composition as described herein. In some aspects, the isolated simukunin polypeptide includes an amino acid sequence at least about 95% identical to SEQ ID NO:3 and wherein the isolated simukunin polypeptide inhibits Factor Xa, elastase, and cathepsin G. In some aspect, administration is parenteral. In some aspects, administration is topical.

The present invention includes a method of modulating the function of neutrophils, macrophages, and/or mast cells in a subject, the method including administering to the subject an isolated simukunin polypeptide as described herein or a composition as described herein. In some aspects, the isolated simukunin polypeptide includes an amino acid sequence at least about 95% identical to SEQ ID NO:3 and wherein the isolated simukunin polypeptide inhibits Factor Xa, elastase, and cathepsin G. In some aspect, administration is parenteral. In some aspects, administration is topical.

The present invention includes a method of inhibiting plasma coagulation and inhibiting elastase and/or cathepsin G in a subject, the method including administering to the subject an isolated simukunin polypeptide as described herein or a composition as described herein. In some aspects, the isolated simukunin polypeptide includes an amino acid sequence at least about 95% identical to SEQ ID NO:3 and wherein the isolated simukunin polypeptide inhibits Factor Xa, elastase, and cathepsin G. In some aspect, administration is parenteral. In some aspects, administration is topical.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIGS. 1A and 1B. SV-66 and SV-170 belong to the Kunitz family of protease inhibitors. FIG. 1A shows nucleotide sequences of SV-66 (SEQ ID NO:1) and SV-170 (SEQ ID NO:4) and the translated polypeptide sequences of SV-66 and SV-170. Start and stop codons are in white with black shading. Numbers below the amino acid residues are designated based on the putative mature protein. Signal sequences predicted by SignalP are underlined. SV-66 encodes a 102 amino-acid polypeptide (Simukunin) (SEQ ID NO:2), which includes a 19 amino-acid N-terminal signal sequence. Mature Simukunin is predicted to consist of 83 amino-acid residues (SEQ ID NO:3), with a theoretical mass of 9627.22 Da and pI of 9.93. SV-66 also contains a putative O-glycosylation site at position 81 (Ser). SV-170 encodes a 78 amino-acid polypeptide (SEQ ID NO:5), which includes an N-terminal 22 amino-acid signal sequence. Mature SV-170 is predicted to consist of 56 amino-acid residues (SEQ ID NO:6), and theoretical mass and pI are 6526.66 Da and 8.87, respectively. FIG. 1B shows alignment of representative Kunitz domain sequences with SV-66 (SEQ ID NO:7) and SV-170 (SEQ ID NO:8). Each Kunitz domain was separated from the original sequences for alignment (numbers denote amino-acid positions in the original mature peptides). All reference sequences were retrieved from GenBank. Accession numbers are as follows: Accession number P10646 for TFPI (human: three Kunitz domains—KU1 (SEQ ID NO:9), KU2 (SEQ ID NO:10), and KU3 (SEQ ID NO:11)); Accession number AM49369 for BPTI (*Bos taurus*: one Kunitz domain (SEQ ID NO:12)); Accession number AAR97367 for Amblin (*Amblyomma hebraeum*: two Kunitz domains—KU1 (SEQ ID NO:13) and KU2 (SEQ ID NO:14)); and Accession number CAC82583 for Boophilin (*Rhipicephalus microplus*: two Kunitz domains—KU1 (SEQ ID NO:15) and KU2 SEQ ID NO:16). Strictly conserved cysteine residues are indicated with white arrows, and predicted conserved disulfide bonds are shown in solid lines. The reactive site loop (RSL) $P_4$-$P_{2'}$ residues, conserved in canonical binding inhibitors, are indicated by asterisks. The $P_1$ residue is indicated with a black arrow. Highly conserved $P_1$-$P_{1'}$ (Arg/Lys-Ala/Gly) residues are shaded and boxed. Other identical residues across the domain are shaded and indicated with a plus (+) and conserved or semi-conserved residues are shaded with grey.

FIG. 2A shows sex and tissue-specific expression of Simukunin. Transcript was detected in the adult female body (head and thorax without abdomen), but not in adult female carcasses (bodies without salivary glands or heads). M: male; F: mature female; NTC: no-template control. Five individuals were pooled for each sample. Actin PCR products are shown as a positive control indicating equivalent concentrations of template among samples. Each panel is a composite of two rows (upper and lower) of wells, run in the same gel at the same time. FIG. 2B shows a time-course of expression of Simukunin. Transcript was detected before, and at selected time points up to 48 h post blood meal. Fresh: freshly eclosed non-blood-fed female adult; hpbf: hours post blood feeding; NTC: no-template control. Two samples, each comprised of five pooled individuals, were analyzed for each time point.

FIGS. 6A to 6C. rSimukunin displays high-affinity binding to FXa and elastase. FIG. 6A shows surface Plasmon Resonance (SPR) Sensorgrams show mouse, bovine, and human FXa, the FXa derivatives des-GLA-hFXa and DEGR-hFXa, and other coagulation factors (all tested at 200 nM) binding to immobilized rSimukunin. FIG. 6B shows sensorgrams for various concentrations of human FXa (50 nM, 25 nM, 12.5 nM, 6.25 nM, and 3.1 nM) binding to immobilized rSumukunin. FIG. 6C shows sensorgrams for various concentrations of elastase (3.75 nM, 1.8 nM, 0.9 nM, and 0.45 nM) binding to immobilized rSimukunin. Data were fitted using a 1:1 binding model (Langmuir). RU: resonance units.

DETAILED DESCRIPTION OF ILLUSTRATIVE EMBODIMENTS OF THE PRESENT INVENTION

Figure 2A:
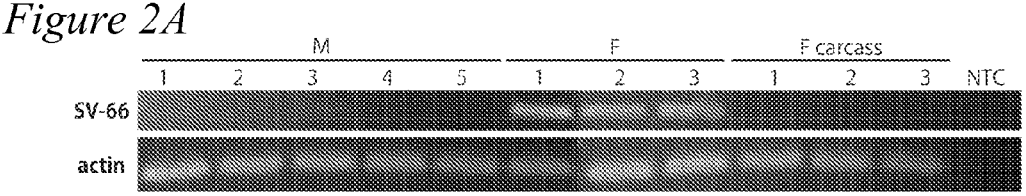
FIGS. 2A and 2B. SV-66 is constitutively expressed in the salivary glands of adult female *S. vittatum*.

The present invention includes a novel protein, also referred to herein as simukunin, isolated from salivary glands of a blood-feeding fly (*Simulium vittatum*), that inhibits the function of several physiologically important enzymes. Simukunin is a potent inhibitor of the blood coagulation cascade, inhibiting Factor Xa, and to a lesser extent, inhibiting Factor XIa, and functioning as an efficient anticoagulant. Simukunin also inhibits elastase and cathepsin G, which play important roles in mast cell and neutrophil-driven inflammation. Accordingly, simukunin is a potent anticoagulant, with additional anti-inflammatory properties.

The present invention includes an isolated simukunin polypeptide, and fragments and derivatives thereof. Such a simukunin polypeptide, or fragment or derivative thereof, may exhibit one or more of the physical or functional characteristics described herein.

In some embodiments, a simukunin polypeptide may have at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% amino acid identity to a simukunin amino acid sequence as described herein. For example, a simukunin polypeptide may have at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% amino acid identity to SEQ ID NO:2 or SEQ ID NO:3, or a fragment thereof.

In some embodiments, a simukunin polypeptide is encoded by a polynucleotide sequence with at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to SEQ ID NO:1.

In some embodiments, a simukunin polypeptide is encoded by a polynucleotide sequence that hybridizes under "stringent conditions," also referred to herein as "high stringency conditions," to a polynucleotide sequence described herein. For example, hybridizing under stringent conditions to SEQ ID NO:1.

Also included in the present invention are isolated *Simulium vittatum* SV-170 polypeptides, and fragments and derivatives thereof. Such a *Simulium vittatum* SV-170 polypeptide or fragment of derivative thereof may demonstrate one of more of the physical or functional characteristic of a *Simulium vittatum* SV-170 polypeptide, as described herein.

In some embodiments, a *Simulium vittatum* SV-170 polypeptide may have at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% amino acid identity to a *Simulium vittatum* SV-170 amino acid sequence as described herein. For example, a *Simulium vittatum* SV-170 polypeptide may have at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% amino acid identity to SEQ ID NO:5 or SEQ ID NO:6, or a fragment thereof.

In some embodiments, a *Simulium vittatum* SV-170 polypeptide is encoded by a polynucleotide sequence with at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to SEQ ID NO:4.

In some embodiments, a *Simulium vittatum* SV-170 polypeptide is encoded by a polynucleotide sequence that hybridizes under "stringent conditions," also referred to herein as "high stringency conditions," to a polynucleotide sequence described herein. For example, hybridizing under stringent conditions to SEQ ID NO:4.

Also included in the present invention are fragments of a polypeptide described herein. A fragment may be, for example, include about any 5, about any 10, about any 15, about any 20, about any 25, about any 30, about any 35, about any 40, about any 45, about any 50, about any 55, about any 60, about any 65, about any 70, about any 75, about any 80, about any 85, about any 90, about any 95, about any 95, or about any 100 consecutive amino acids of a polypeptide described herein, or any range thereof. For example, a fragment may include about any 10, about any 15, about any 20, about any 25, about any 30, about any 35, about any 40, about any 45, about any 50, about any 55, about any 60, about any 65, about any 70, about any 75, about any 80, about any 85, about any 90, about any 95, about any 95, or about any 100 consecutive amino acids of SEQ ID NO:2, SEQ ID NO:3, SEQ ID NO:5, or SEQ ID NO:6, or any range thereof.

Also included in the present invention are polypeptides, and derivatives, or fragments thereof, as described herein with additional amino acid residues not of simukunin, SV-170, and/or *Simulium vittatum*. Such heterologous sequences may, for example, encode additional enzymatic activities or other additional components, such as, for example, a linker, an immunogenic carrier protein, a detectable marker, or a fusion protein.

A polypeptide of the present invention may possess one or more of the physical characteristics described herein. For example, a polypeptide of the present invention may include one or more of the residues characteristic of a Kunitz domain. This includes, but is not limited to, one or more of the characteristic residues identified in FIG. 1B. For example, a polypeptide may include one, two, three, four, five, or six of the strictly conserved cysteine residues (for example, represented by amino acids 5, 14, 30, 38, 51, and 55 of SEQ ID NO:3, respectively); one, two, or three of the conserved disulfide bonds characteristic of a Kunitz domain (represented by disulfide bonds between cysteine residues C5 to C55, C14 to C38, and C30 to C51 of SEQ ID NO:3); one, two, three, four, five, or six of the conserved amino acid residues of the reactive site loop (RSL) $P_4$-$P_{2'}$ residues (for example, represented by amino acid positions 12, 13, 14, 15, 16, and 17 of SEQ ID NO:3); a basic residue, such as, for example, Arg (R) or Lys (K), at site $P_1$ (represented by amino acid position 15 of SEQ ID NO:3); and/or an Ala (A) or Gly (G) at site $P_1$ (for example, represented by amino acid position 16 of SEQ ID NO:3).

A polypeptide of the present invention may possess one or more of the functional characteristics described herein. For example, a polypeptide described herein may demonstrate anticoagulant activity, anti-clotting activity, anti-platelet activity, anti-inflammatory activity, and/or immunomodulating activity. A polypeptide described herein may inhibit the function of one or more enzymes. A polypeptide as described herein may be a protease inhibitor, including but not limited to, a serine protease inhibitor. In some embodiments, a polypeptide of the present invention inhibits multiple proteases. Such an enzyme may be, for example, a mammalian enzyme, from, for example, human, mouse, rat, bovine, and/or non-human primates. Such an enzyme may be, for example, a bacterial or parasitic enzyme.

A polypeptide described herein may inhibit Factor Xa enzymatic activity. In some embodiments, such a polypeptide inhibits one or more additional serine proteases, for example, one or more of elastase, cathepsin G, plasmin, Factor IXa, Factor XIa, kallikrein, trypsin, β-tryptase, chymase, α-chymotrypsin, and/or enterokinase.

A polypeptide of the present invention may inhibit the enzymatic activity of one or more of Factor Xa, elastase, cathepsin G, plasmin, Factor IXa, Factor Xa, Factor XIa, kallikrein, trypsin, β-tryptase, chymase, α-chymotrypsin, and/or enterokinase.

A polypeptide of the present invention may bind to Factor Xa and/or elastase.

In some embodiments, a polypeptide of the present invention does not inhibit, bind, and/or effect enzymatic activity or function of one or more of Factor XIIa, thrombin, matriptase, u-Pa and/or t-PA.

A polypeptide of the present invention may inhibit, reduce, or slow blood coagulation and/or may inhibit plasma coagulation. A polypeptide of the present invention may inhibit an inflammatory response. A polypeptide of the present invention may inhibit or reduce mast and or neutrophil driven inflammatory processes, for example, by inhibiting the enzymatic activity of an enzyme contained in or released from a neutrophil, a mast cell, or other immune cell.

The functional characterization of a polypeptide of the present invention may be by any of a variety of available methods, including, but not limited to, any of those described in the examples section included herewith. In some embodiments, a measure of the enzymatic inhibition and/or binding of a polypeptide may be about any or more of those measurements (such as concentrations, ratios, $IC_{50}$, $K_i$, $K_m$, $K_d$) described in the examples section included herewith.

As used herein, the term "polypeptide" refers broadly to a polymer of two or more amino acids joined together by peptide bonds, regardless of length or post-translational modification. It should be understood that these terms do not connote a specific length of a polymer of amino acids, nor are they intended to imply or distinguish whether the polypeptide is produced using recombinant techniques, chemical or enzymatic synthesis, or is naturally occurring.

As used herein, "identity" refers to sequence similarity between two polypeptides or two polynucleotides. The sequence similarity between two polypeptides is determined by aligning the residues of the two polypeptides (e.g., a candidate amino acid sequence and a reference amino acid sequence, such as SEQ ID NO:2, 3, 5, or 6, or a portion thereof) to optimize the number of identical amino acids along the lengths of their sequences; gaps in either or both sequences are permitted in making the alignment in order to optimize the number of shared amino acids, although the amino acids in each sequence must nonetheless remain in their proper order. The sequence similarity is typically at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity. Sequence similarity may be determined, for example, using sequence techniques such as the BESTFIT algorithm in the GCG package (Madison Wis.), or the Blastp program of the BLAST 2 search algorithm, as described by Tatusova, et al. (*FEMS Microbiol Lett* 1999, 174:247-250), and available through the World Wide Web, for instance at the internet site maintained by the National Center for Biotechnology Information, National Institutes of Health. Preferably, sequence similarity between two amino acid sequences is determined using the Blastp program of the BLAST 2 search algorithm. Preferably, the default values for all BLAST 2 search parameters are used, including matrix=BLOSUM62; open gap penalty=11, extension gap penalty=1, gap x_dropoff=50, expect=10, wordsize=3, and optionally, filter on. In the comparison of two amino acid sequences using the BLAST search algorithm, structural similarity is referred to as "identities."

The sequence similarity between two polynucleotides is determined by aligning the residues of the two polynucleotides (e.g., a candidate nucleotide sequence and a reference nucleotide sequence, such as SEQ ID NO:1, 3, 5, 7, or a portion thereof) to optimize the number of identical nucleotides along the lengths of their sequences; gaps in either or both sequences are permitted in making the alignment in order to optimize the number of shared nucleotides, although the nucleotides in each sequence must nonetheless remain in their proper order. The sequence similarity is typically at least 80% identity, at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, or at least 99% identity. Sequence similarity may be determined, for example, using sequence techniques such as GCG FastA (Genetics Computer Group, Madison, Wis.), MacVector 4.5 (Kodak/IBI software package) or other suitable sequencing programs or methods known in the art. Preferably, sequence similarity between two nucleotide sequences is determined using the Blastn program of the BLAST 2 search algorithm, as described by Tatusova, et al. (1999, *FEMS Microbiol Lett.*, 174:247-250), and available through the World Wide Web, for instance at the internet site maintained by the National Center for Biotechnology Information, National Institutes of Health. Preferably, the default values for all BLAST 2 search parameters are used, including reward for match=1, penalty for mismatch=−2, open gap penalty=5, extension gap penalty=2, gap x_dropoff=50, expect=10, wordsize=11, and optionally, filter on. In the comparison of two nucleotide sequences using the BLAST search algorithm, sequence similarity is referred to as "identities."

Conditions that "allow" an event to occur or conditions that are "suitable" for an event to occur, such as an enzymatic reaction, or "suitable" conditions are conditions that do not prevent such events from occurring. Thus, these conditions permit, enhance, facilitate, and/or are conducive to the event.

The present invention includes an isolated polynucleotide sequence encoding a simukunin polypeptide as described herein, and fragments and derivatives thereof. Such a simukunin polypeptide, or fragment or derivative thereof, may have one or more of the functional characteristics described herein. Also included are isolated polynucleotide sequences encoding a *Simulium vittatum* SV-170 polypeptide as described herein, and fragments and derivatives thereof. Such a *Simulium vittatum* SV-170 polypeptide or fragment of derivative thereof may demonstrate one of more of the functional characteristic of a *Simulium vittatum* SV-170 polypeptide, as described herein.

In some embodiments, a polynucleotide sequence of the present invention may have at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to a polynucleotide sequence described herein. For example, a derivative thereof may have at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% sequence identity to SEQ ID NO:1 or SEQ ID NO:4, or a fragment thereof.

In some embodiments, a polynucleotide sequence of the present invention may encode a polypeptide as described herein. For example, a polynucleotide sequence of the present invention may encode an amino acid sequence with at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% sequence identity SEQ ID NO:3 or SEQ ID NO:6.

Two polynucleotide sequences may be compared using the Blastn program of the BLAST 2 search algorithm, as described by Tatusova and Madden, 1999, FEMS Microbiol Lett; 174:247-250), and available on the world wide web at ncbi.nlm.nih.gov/gorf/bl2.html. Preferably, the default values for all BLAST 2 search parameters are used, including reward for match=1, penalty for mismatch=−2, open gap penalty=5, extension gap penalty=2, gap x_dropoff=50, expect=10, wordsize=11, and filter on.

In some embodiments, a polynucleotide sequence of the present invention is a polynucleotide sequence that hybridizes under "stringent conditions," also referred to herein as "high stringency conditions," to a polynucleotide sequence described herein. For example, hybridizing under stringent conditions to SEQ ID NO:1 or SEQ ID NO:4. The polypeptide encoded by such a polynucleotide sequence may exhibit one or more of the various physical and/or functional characteristics described herein. Stringency of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures.

Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995). "Stringent conditions" or "high stringency conditions," as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

An isolated polynucleotide of the present invention may include additional sequences not of simukunin origin. Such heterologous sequences may, for example, encode additional enzymatic activities or other additional components, such as promoter, transcription initiation, and/or and termination sequences.

The present invention also includes recombinant vectors including an isolated polynucleotide as described herein. A wide variety of plasmid and viral vectors are known in the art. The appropriate DNA sequence can be inserted into a vector by a variety of procedures. In general, the DNA sequence is inserted into an appropriate restriction endonuclease site(s) in a vector by procedures known in the art. Such procedures are deemed to be within the scope of those skilled in the art. Large numbers of suitable vectors and promoters are known to those of skill in the art, and are commercially available. The following vectors are provided by way of example. Bacterial vectors include, for example, pQE70, pQE60, pQE-9, pBS, pD10, phagescript, psiX174, pbluescript SK, pbsks, pNH8A, pNH16a, pNH18A, pNH46A, ptrc99a, pKK223-3, pKK233-3, pDR540, and pRIT5. Eukaryotic vectors include, for example, pWLNEO, pSV2CAT, pOG44, pXT1, pSG, pSVK3, pBPV, pMSG, and pSVL. However, any other plasmid or vector can be used. A large number of such vectors have been described in various publications and many such vectors are commercially available.

Included with the present invention are host cells that incorporate an isolated polynucleotide sequence encoding a simukunin polypeptide, or derivative or fragment thereof, and host cells that incorporate a vector incorporating an isolated polynucleotide sequence encoding a simukunin polypeptide, or derivative or fragment thereof. A host cell can be a higher eukaryotic cell, such as a mammalian or insect cell, or a lower eukaryotic cell, such as a yeast cell. Or, the host cell can be a prokaryotic cell, such as a bacterial cell, or a plant cell. Introduction of a vector construct into the host cell can be effected by any suitable techniques, such as, for example, calcium phosphate transfection, DEAE-Dextran mediated transfection, or electroporation.

As used herein, the term "polynucleotide" refers to a polymeric form of nucleotides of any length, either ribonucleotides or deoxynucleotides, and includes both double- and single-stranded RNA and DNA. A polynucleotide can be obtained directly from a natural source, or can be prepared with the aid of recombinant, enzymatic, or chemical techniques. A polynucleotide can be linear or circular in topology. A polynucleotide may be, for example, a portion of a vector, such as an expression or cloning vector, or a fragment. A polynucleotide may include nucleotide sequences having different functions, including, for instance, coding regions, and non-coding regions such as regulatory regions.

As used herein, the terms "coding region" and "coding sequence" are used interchangeably and refer to a nucleotide sequence that encodes a polypeptide and, when placed under the control of appropriate regulatory sequences, expresses the encoded polypeptide. The boundaries of a coding region are generally determined by a translation start codon at its 5' end and a translation stop codon at its 3' end. A "regulatory sequence" is a nucleotide sequence that regulates expression of a coding sequence to which it is operably linked. Non-limiting examples of regulatory sequences include promoters, enhancers, transcription initiation sites, translation start sites, translation stop sites, and transcription terminators. The term "operably linked" refers to a juxtaposition of components such that they are in a relationship permitting them to function in their intended manner. A regulatory sequence is "operably linked" to a coding region when it is joined in such a way that expression of the coding region is achieved under conditions compatible with the regulatory sequence.

A polynucleotide that includes a coding region may include heterologous nucleotides that flank one or both sides of the coding region. As used herein, "heterologous nucleotides" refer to nucleotides that are not normally present flanking a coding region that is present in a wild-type cell. For instance, a coding region present in a wild-type cell and encoding an HCN polypeptide is flanked by homologous sequences, and any other nucleotide sequence flanking the coding region is considered to be heterologous. Examples of heterologous nucleotides include, but are not limited to regulatory sequences. Typically, heterologous nucleotides are present in a polynucleotide of the present invention through the use of standard genetic and/or recombinant methodologies well known to one skilled in the art. A polynucleotide of the present invention may be included in a suitable vector.

As used herein, an "exogenous polynucleotide" refers to a polynucleotide that has been introduced into a cell by artificial means. As used herein, the term "endogenous polynucleotide" refers to a polynucleotide that is normally or naturally found in a cell. An "endogenous polynucleotide" is also referred to as a "native polynucleotide."

The terms "complement" and "complementary" as used herein, refer to the ability of two single stranded polynucleotides to base pair with each other, where an adenine on one strand of a polynucleotide will base pair to a thymine or uracil on a strand of a second polynucleotide, and a cytosine on one strand of a polynucleotide will base pair to a guanine on a strand of a second polynucleotide. Two polynucleotides are complementary to each other when a nucleotide sequence in one polynucleotide can base pair with a nucleotide sequence in a second polynucleotide. For instance, 5'-ATGC and 5'-GCAT are complementary. The term "substantial complement" and cognates thereof as used herein, refer to a polynucleotide that is capable of selectively hybridizing to a specified polynucleotide under stringent hybridization conditions.

The present invention includes compositions including one or more isolated polypeptides or polynucleotides as described herein. In a preferred form, an isolated polypeptide is purified and substantially free of other agents. As used herein, an "isolated" substance is one that has been removed from its natural environment, produced using recombinant techniques, or chemically or enzymatically synthesized. For instance, a polypeptide, a polynucleotide, or a cell can be isolated. Preferably, a substance is purified, i.e., is at least 60% free, preferably at least 75% free, and most preferably at least 90% free from other components with which they are naturally associated.

Compositions may be administered in any of the methods described herein and may be formulated in a variety of forms adapted to the chosen route of administration. The formulations may be conveniently presented in unit dosage form and may be prepared by methods well known in the art of pharmacy. A composition may include a pharmaceutically acceptable carrier. The term "pharmaceutically acceptable," as used herein, means that the compositions or components thereof so described are suitable for physiological contact with a subject without undue toxicity, incompatibility, instability, allergic response, and the like. A composition may be a pharmaceutical composition.

The preparation of such compositions is well understood in the art. The formulations of this invention may include one or more accessory ingredients including, but not limited to, diluents, buffers, binders, disintegrants, surface active agents, thickeners, lubricants, preservatives, including, for example, antioxidants, and the like. Pharmaceutically acceptable includes salts, amides and esters that are well known in the art. Representative acid addition salts include, for example, hydrochloride, hydrobromide, sulfate, bisulfate, acetate, oxalate, valerate, oleate, palmitate, stearate, laurate, borate, benzoate, lactate, phosphate, toluenesulfonate, methanesulfonate, citrate, maleate, fumarate, succinate, tartrate, ascorbate, glucoheptonate, lactobionate, lauryl sulfate salts, and the like. Representative alkali or alkaline earth metal salts include, for example, aluminum, calcium, lithium, magnesium, potassium, sodium, or zinc salt, an ammonium salt such as a tertiary amine or quaternary ammonium salt, and an acid salt such as a succinate, tartarate, bitartarate, dihydrochloride, salicylate, hemisuccinate, citrate, isocitrate, malate, maleate, mesylate, hydrochloride, hydrobromide, phosphate, acetate, carbamate, sulfate, nitrate, formate, lactate, gluconate, glucuronate, pyruvate, oxalacetate, fumarate, propionate, aspartate, glutamate, or benzoate salt, and the like. Pharmaceutically acceptable carriers includes, for example, non-toxic, inert solid, semi-solid or liquid filler, diluent, encapsulating material or formulation auxiliary of any type. Examples of materials that may serve as pharmaceutically acceptable carriers include, but are not limited to, sugars, such as, for example, lactose, glucose and sucrose, starches such as, for example, corn starch and potato starch, cellulose and its derivatives such as, for example, sodium carboxymethyl cellulose, ethyl cellulose and cellulose acetate, powdered tragacanth, malt, gelatin, talc, excipients such as, for example, cocoa butter and suppository waxes, oils such as, for example, peanut oil, cottonseed oil, safflower oil, sesame oil, olive oil, corn oil and soybean oil, glycols, such as, for example, propylene glycol, polyols such as, for example, glycerin, sorbitol, mannitol and polyethylene glycol, esters such as, for example, ethyl oleate and ethyl laurate, agar, buffering agents such as, for example, magnesium hydroxide and aluminum hydroxide, alginic acid, pyrogen-free water, isotonic saline, Ringer's solution, ethyl alcohol and phosphate buffer solutions, as well as other non-toxic compatible substances used in pharmaceutical formulations. Wetting agents, emulsifiers and lubricants such as, for example, sodium lauryl sulfate and magnesium stearate, as well as coloring agents, releasing agents, coating agents, sweetening, flavoring and perfuming agents, preservatives and antioxidants may also be present in the composition, according to the judgment of the formulator.

For parenteral administration in an aqueous solution, the solution may be suitably buffered if necessary and the liquid diluent first rendered isotonic with sufficient saline or glucose. For enteral administration, the inhibitor may be administered in a tablet or capsule, which may be enteric coated, or in a formulation for controlled or sustained release. Many suitable formulations are known, including polymeric or microparticles or nanoparticles encapsulating drug to be released, ointments, gels, or solutions which can be used topically or locally to administer drug, and even patches, which provide controlled release over a prolonged period of time. These can also take the form of implants. Compositions for nasal administration may be formulated for aerosol or inhalation administration. Such compositions may include solutions in saline which may also contain, for example, benzyl alcohol or other suitable preservatives, absorption promoters to enhance bioavailability, and/or other solubilizing or dispersing agents such as those known in the art. Compositions for rectal administration include, for example, suppositories which may contain a suitable non-irritating excipient, such as cocoa butter, synthetic glyceride esters or polyethylene glycols, which are solid at ordinary temperatures, but liquify and/or dissolve in the rectal cavity to release the drug.

For human and veterinary administration, compositions of the present invention may meet sterility, pyrogenicity, and general safety and purity standards as required by federal regulatory agencies, such as the FDA. Such compositions are considered suitable for parenteral or enteral administration to a mammal. Such compositions may be pyrogen-free.

Certain medical conditions, such as strokes and some cardiovascular blockages, involve both clot formation and inflammation. A simukunin polypeptide as described herein may be used in the treatment for these conditions. For example, administered in the early stages of a medical crisis, the protein may limit damage by antagonizing clot formation and inflammatory responses in the affected tissue.

A polypeptide as described herein may be used to inhibit the function of one or more enzymes. For example, a polypeptide as described herein may be used to inhibit the activity of one or more serine proteases. For example, a polypeptide as described herein may be used in methods to inhibit Factor Xa enzymatic activity. A polypeptide as described herein may be used in methods to inhibit elastase and/or cathepsin G. A polypeptide as described herein may be used in methods to inhibit Factor Xa, elastase, and cathepsin G. A polypeptide as described herein may be used in methods to inhibit one or more additional serine proteases, such as for example, one or more of plasmin, Factor IXa, Factor XIa, kallikrein, trypsin, β-tryptase, chymase, α-chymotrypsin, and/or enterokinase.

A polypeptide as described herein may be used in methods to inhibit the enzymatic activity of one or more of Factor Xa, elastase, cathepsin G, plasmin, Factor IXa, Factor XIa, kallikrein, trypsin, β-tryptase, chymase, α-chymotrypsin, and/or enterokinase.

As used herein, the term "inhibit" means prevent, decrease, or reverse. Such contact may be in vitro, ex vivo, and/or in vivo. As used herein in vitro is in cell culture, ex vivo is a cell that has been removed from the body of a subject, and in vivo is within the body of a subject.

The present invention provides for the use of a polypeptide as described herein as an anticoagulant and/or anti-inflammatory agent. Such an agent may demonstrate anticoagulant activity, anti-clotting activity, anti-platelet activity, anti-inflammatory activity, and/or immunomodulating activity. As used herein, an anticoagulant agent prevents the coagulation (clotting) of blood or plasma.

A polypeptide as described herein may be used in the treatment of various medical conditions that are treated with the administration of an anticoagulant, to prevent the formation of blood clots and the extension of existing clots. Examples include, but are not limited to, strokes, cardiovascular blockages, deep vein thrombosis, myocardial infarction, pulmonary embolism, venous thromboembolism, congestive heart failure, atrial fibrillation, and genetic or acquired hypercoagulability. A polypeptide as described herein may be administered to a subject to prevent, discourage, minimize, or slow the rate of formation of blood clots. A polypeptide as described herein may be administered to a subject after a blood clot has formed and the anti-coagulant activity of the polypeptide destroying or dissolving the clot.

In some applications, a polypeptide as described herein may be used to coat or treat various laboratory instruments or devices, including, but not limited to, blood transfusion bags, test tubes used for laboratory blood tests, and medical and surgical equipment, to prevent the formation of blood clots on the surface or within.

The present invention includes methods of modulating inflammation. Modulation may include inhibiting or reducing inflammation and/or reducing or inhibiting tissue damage from inflammatory processes. The serine proteases elastase and cathepsin G are implicated in the host defense against invading bacterial and fungal pathogens, participating in the killing and digestion of engulfed pathogens. Both elastase and cathepsin G are secreted by activated neutrophils and play important roles in the inflammatory response. Elastase and cathepsin G regulate the ability of immune cells known as neutrophils to secrete chemicals that attract other immune cells and start the local inflammatory process. Over time, the excessive accumulation of immune cells can lead to tissue and cartilage damage in joints, causing pain and limiting mobility. See for example, the review by Pham, 2006, *Nat Rev Immunol;* 6(7):541-50 ("Neutrophil serine proteases: specific regulators of inflammation"). A polypeptide as described herein may be used in methods to inhibit the enzymatic activity of one or more serine proteases, such as elastase and/or cathepsin G. Such inhibition may reduce the tissue damage associated with elastase and/or cathepsin G release. A polypeptide as described herein may be used in methods to modulate the function of immune cells such as neutrophils, macrophages, monocytes, and/or mast cells. A polypeptide as described herein may be used in the treatment of conditions in which the pathology is associated with elastase and/or cathepsin G enzymatic activity, such as for example, in the treatment of pulmonary emphysema, $\alpha_1$-antitrypsin deficiency, cystic fibrosis, rheumatoid arthritis, keratoconus, asthma, allergies, eczema, and cancer. In some applications, a simukunin polypeptide as described herein may be administered the form of a topical treatment to manage inflammatory conditions of the skin.

A polypeptide as described herein may be used in methods of modulating both coagulation and inflammation, including, but not limited to modulation of any two, three, four, five, six, or more activities described herein.

A polypeptide as described herein may be used in methods of inhibiting the enzymatic activity of one or more of plasmin, Factor IXa, Factor XIa, kallikrein, trypsin, β-tryptase, chymase, α-chymotrypsin, and/or enterokinase and methods of inhibiting a pathology associated with the expression of such an enzyme in the tissues of a subject.

With the methods of the present invention, any of a variety of modes of administration may be used. For example, administration may be intravenous, topical, oral, rectal, intranasal, subcutaneous, intraperitoneal, intramuscular, intracardiac, intraosseous, intracerebral, intrathecal, epidural, transdermal, subcutaneous, intracavernous, intravitreal, intra-articular, intrasynovial, transscleral, or intratumor. In some aspects, administration is parenteral, that is, administration into the body is via a route other than the gastro-intestinal tract, An agent of the present disclosure may be administered at once, or may be divided into a number of multiple doses to be administered at intervals of time. For example, agents of the invention may be administered repeatedly, e.g., at least 2, 3, 4, 5, 6, 7, 8, or more times, or may be administered by continuous infusion. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that any concentration ranges set forth herein are exemplary only and are not intended to limit the scope or practice of the claimed compositions and methods.

By a "therapeutically effective amount" is meant a sufficient amount of the compound to treat the subject at a reasonable benefit/risk ratio applicable to obtain a desired therapeutic response. It will be understood, however, that the total daily usage of the compounds and compositions of the present invention will be decided by the attending physician within the scope of sound medical judgment. The specific therapeutically effective dose level for any particular patient will depend upon a variety of factors including, for example, the disorder being treated and the severity of the disorder, activity of the specific compound employed, the specific composition employed, the age, body weight, general health, sex and diet of the patient, the time of administration, route of administration, and rate of excretion of the specific compound employed, the duration of the treatment, drugs used in combination or coincidentally with the specific compound employed, and like factors well known in the medical arts.

In some therapeutic embodiments, an "effective amount" of an agent is an amount that results in a reduction of at least one pathological parameter. Thus, for example, in some aspects of the present disclosure, an effective amount is an amount that is effective to achieve a reduction of at least about 10%, at least about 15%, at least about 20%, or at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, compared to the expected reduction in the parameter in an individual not treated with the agent.

In accordance with the present invention, a simukunin polypeptide may be administered in combination with the administration of one or more previously known treatment modalities. As used herein, the term "additional therapeutic agent" represents one or more agents previously known to be effective in the treatment of conditions for which the administration of an anti-coagulant or an anti-inflammatory agent is appropriate. In some embodiments of the present invention, the administration of a simukunin polypeptide in combination with additional therapeutic agents may demonstrate therapeutic synergy. As used herein, a combination may demonstrate therapeutic synergy if it is therapeutically superior to one or other of the constituents used at its optimum dose. In some embodiments, a combination demonstrates therapeutic synergy if the efficacy of a combination is characterized as more than additive actions of each constituent. The administration of a simukunin polypeptide may take place before, during, and/or after the administration of the other mode of therapy. The present invention includes methods of administering one or more simukunin polypeptides in combination with the administration of one or more previously known treatment modalities. The present invention also includes compositions of one or more simukunin polypeptides and one or more previously known treatment modalities.

As used herein, the term "subject" includes, but is not limited to, humans and non-human vertebrates. In preferred embodiments, a subject is a mammal, particularly a human. A subject may be an individual. A subject may be an "individual," "patient," or "host." Non-human vertebrates include livestock animals, companion animals, and laboratory animals. Non-human subjects also include non-human primates as well as rodents, such as, but not limited to, a rat or a mouse. Non-human subjects also include, without limitation, chickens, horses, cows, pigs, goats, dogs, cats, guinea pigs, hamsters, ferrets, mink, and rabbits.

As used herein "in vitro" is in cell culture and "in vivo" is within the body of a subject. As used herein, "isolated" refers to material that has been either removed from its natural environment (e.g., the natural environment if it is naturally occurring), produced using recombinant techniques, or chemically or enzymatically synthesized, and thus is altered "by the hand of man" from its natural state.

The present invention also includes methods of making and using the polypeptides, polynucleotides, and compositions described herein.

The term "and/or" means one or all of the listed elements or a combination of any two, three, four, five, or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

The description exemplifies illustrative embodiments. In several places throughout the application, guidance is provided through lists of examples, which examples can be used in various combinations. In each instance, the recited list serves only as a representative group and should not be interpreted as an exclusive list.

All headings are for the convenience of the reader and should not be used to limit the meaning of the text that follows the heading, unless so specified.

The present invention is illustrated by the following examples. It is to be understood that the particular examples, materials, amounts, and procedures are to be interpreted broadly in accordance with the scope and spirit of the invention as set forth herein.

EXAMPLES

Example 1

Simukunin from the Salivary Glands of the Black Fly *Simulium vittatum* Inhibits Enzymes that Regulate Clotting and Inflammatory Responses Black flies (Diptera: Simuliidae) feed on blood, and are important vectors of *Onchocerca volvulus*, the etiolytic agent of River Blindness. Blood feeding depends on pharmacological properties of saliva, including anticoagulation, but the molecules responsible for this activity have not been well characterized. Two Kunitz family proteins, SV-66 and SV-170, were identified in the sialome of the black fly *Simulium vittatum*. As Kunitz proteins are inhibitors of serine proteases, SV-66 and SV-170 are candidate proteins responsible for the anticoagulant activity of black fly saliva. This example demonstrates that only recombinant (r) SV-66, but not rSV-170, inhibited plasma coagulation. Mutational analysis suggested that SV-66 is a canonical BPTI-like inhibitor. Functional assays indicated that rSV66 reduced the activity of ten serine proteases, including several involved in mammalian coagulation. rSV-66 most strongly inhibited the activity of Factor Xa, elastase, and cathepsin G, exhibited lesser inhibitory activity against Factor IXa, Factor XIa, and plasmin, and exhibited no activity against Factor XIIa and thrombin. Surface plasmon resonance studies indicated that rSV-66 bound with highest affinity to elastase ($K_D$=0.4 nM) and to the active site of FXa ($K_D$=3.07 nM). This novel protein has been named "Simukunin." This Example demonstrates that Simukunin preferentially inhibits Factor Xa. The inhibition of elastase and cathepsin G indicate that this protein likely modulates inflammation, which could potentially affect pathogen transmission.

Both eukaryotes and prokaryotes produce Kunitz family protease inhibitors, indicating an ancient origin for Kunitz family encoding genes (Ascenzi et al., 2003, *Curr Protein*

*Pept Sci;* 4:231-251; and Liener, 1986, *J Nutr;* 116:920-923). The most conserved function of Kunitz family proteins is the reversible competitive inhibition of serine proteases (Ascenzi et al., 2003, *Curr Protein Pept Sci;* 4:231-251). A single Kunitz domain is small (about 60 amino acids) and forms a compact globular fold typically containing three disulfide bonds. Based on the structure of bovine pancreatic trypsin inhibitor (BPTI), a typical Kunitz domain contains cysteine residues at positions 5, 14, 30, 38, 51 and 55 in the mature peptide, which form three disulfide bonds C5-055, C14-C38 and C30-C51 (Ascenzi et al., 2003, *Curr Protein Pept Sci;* 4:231-251). The Kunitz domain may exist singly, or as multiple domains within a single polypeptide (Corral-Rodriguez et al., 2009, *Insect Biochem Mol Biol;* 39:579-595). Many Kunitz domains act as protease inhibitors through their scissile bond at positions 15 (P1) and 16 (P1'). The P1 residue is often a basic amino acid (K or R) while the P1' position is an A or G, which together interact with the active site of one or more proteases (Ascenzi et al., 2003, *Curr Protein Pept Sci;* 4:231-251). Alternative modes of action have also been characterized. For example, snake venoms contain Kunitz family proteins named dendrotoxins that exhibit weak anti-protease activity but strongly block neuronal $K^+$ channels (Harvey, 2001, *Toxicon;* 39:15-26).

Blood coagulation in mammals is a physiological response that is activated by a complex enzymatic cascade, consisting primarily of serine proteases, and which terminates with formation of a fibrin clot. Negative regulators of coagulation are primarily protease inhibitors, which include one Kunitz family protein named tissue factor pathway inhibitor (TFPI) (Crawley and Lane, 2008, *Arterioscler Thromb Vasc Biol;* 28:233-242) that inhibits formation of FXa by binding to the FVIIa-Tissue factor-FXa complex (Corral-Rodriguez et al., 2009, *Insect Biochem Mol Biol;* 39:579-595; and Crawley and Lane, 2008, *Arterioscler Thromb Vasc Biol;* 28:233-242). Blood-feeding arthropods also produce anti-hemostatic factors in their saliva, which facilitate blood feeding by interfering with host hemostatic responses (Ribeiro and Francischetti, 2003, *Annu Rev Entomol;* 48:73-88). A variety of anti-coagulation factors have been identified from arthropods including several Kunitz family proteins in the saliva of ticks (Corral-Rodriguez et al., 2009, *Insect Biochem Mol Biol;* 39:579-595; and Francischetti et al., 2009, *Front Biosci;* 14:2051-2088). For example, ixolaris from the deer tick, *Ixodes scapularis*, contains two kunitz domains. The N-terminal Kunitz displays a glutamic acid residue in the P1 position, while the C-terminal Kunitz atypically has only four cysteines (Francischetti et al., 2002, *Blood;* 99:3602-3612). Ixolaris binds to the heparin-binding exosite of coagulation Factor X (FX) and FXa through the C-terminal domain, and this complex forms a tight-binding inhibitor of the FVIIa/Tissue Factor complex. The saliva of *I. scapularis* also contains penthalaris, which has five Kunitz domains and inhibits the tissue factor pathway in a manner similar to ixolaris (Francischetti et al., 2004, *Thromb Haemost;* 91:886-898). Other Kunitz family proteins from tick saliva exhibit functions that range from anti-thrombin and anti-FXa activity to anti-kallikrein and anti-platelet aggregation (Corral-Rodriguez et al., 2009, *Insect Biochem Mol Biol;* 39:579-595); and Maritz-Olivier et al., 2007, *Trends Parasitol;* 23:397-407.

Black flies (Diptera: Simuliidae) like *Simulium vittatum* are small, stout-bodied insects. Females of *S. vittatum* and most other species must feed on blood from a vertebrate host to produce multiple clutches of eggs. Black flies are not only a nuisance for humans and livestock but vector several pathogens including *Onchocerca volvulus* that causes onchocerciasis, (river blindness) in humans, and vesicular stomatitis virus that causes disease in livestock. The bites of *S. vittatum* induce a pronounced and persistent erythema (Cupp et al., 1994, *Am J Trop Med Hyg,* 50:241-246) due to the presence of a salivary protein named *S. vittatum* erythema protein (SVEP) (Cupp et al., 1998, *J Exp Biol;* 201:1553-1561). *S. vittatum* saliva also contains at least three anti-coagulation factors, which exhibit activity against thrombin, FXa, or FV (Jacobs et al., 1990, *Thromb Haemost;* 64:235-238; Abebe et al., 1994, *J Med Entomol;* 31:908-911; Abebe et al., 1995, *J Insect Physiol;* 41:1001-1006; and Abebe et al., 1996, *J Med Entomol;* 33:173-176). The identity of these anti-hemostatic factors, however, remains unknown.

A recent publication on the combined transcriptome and proteome (collectively called the "sialome") of *S. vittatum* salivary glands detected many transcripts and corresponding tryptic peptide fragments including two Kunitz family proteins, named SV-66 and SV-170 (Andersen et al., 2009, *J Proteome Res;* 8(3):1474-1488). In this study, SV-66 and SV-170 were expressed and assessed their anti-coagulant activity. This example demonstrates that SV-66 is an anti-coagulant with anti-FXa activity that also inhibits several other serine proteases.

Results

SV-66 and SV-170 encode conserved Kunitz proteins. SV-66 and SV-170 consist of 309 (SEQ ID NO:1) and 237 (SEQ ID NO:4) nucleotides respectively that encode predicted proteins of 102 (SEQ ID NO:2) and 78 (SEQ ID NO:5) amino acids. FIG. 1A shows nucleotide and translated polypeptide sequences of SV-66 and SV-170. Start and stop codons are in white with black shading. Numbers below the amino acid residues are designated based on the putative mature protein. Signal sequences predicted by SignalP are underlined. SV-66 encodes a 102 amino-acid polypeptide (SEQ ID NO:2) (Simukunin), which includes a 19 amino-acid N-terminal signal sequence. Mature Simukunin is predicted to consist of 83 amino-acid residues (SEQ ID NO:3), with a theoretical mass of 9627.22 Da and pI of 9.93. SV-66 also contains a putative O-glycosylation site at position 81 (Ser). SV-170 encodes a 78 amino-acid polypeptide (SEQ ID NO:5), which includes an N-terminal 22 amino-acid signal sequence. Mature SV-170 is predicted to consist of 56 amino-acid residues (SEQ ID NO:6), and theoretical mass and pI are 6526.66 Da and 8.87, respectively.

FIG. 1B shows alignment of representative Kunitz domain sequences with SV-66 and SV-170. Each Kunitz domain was separated from the original sequences for alignment (numbers denote amino-acid positions in the original mature peptides). All reference sequences were retrieved from GenBank. Accession numbers are: TFPI (human: 3 Kunitz domains), P10646; BPTI (*Bos taurus:* 1 Kunitz domain), AAI49369; Amblin (*Amblyomma hebraeum:* 2 Kunitz domains), AAR97367; Boophilin (*Rhipicephalus microplus:* 2 Kunitz domains), CAC82583. Strictly conserved cysteine residues are indicated with white arrows, and predicted conserved disulfide bonds are shown in solid lines. The reactive site loop (RSL) P4-P2' residues, conserved in canonical binding inhibitors, are indicated by asterisks. The P1 residue is indicated with a black arrow. Highly conserved P1-P1' (Arg/Lys-Ala/Gly) residues are shaded and boxed. Other identical residues across the domain are shaded and indicated with a plus (+) and conserved or semi-conserved residues are shaded with grey.

SignalP identified signal sequences for SV-66 and SV-170 of 19 and 22 amino acids respectively. Residue numbers were assigned based on the predicted mature proteins and indicated signal sequence residues as negative numbers (FIG. 1A). Alignment with selected other Kunitz-domain containing proteins indicated that SV-66 and SV-170 possess six conserved cysteine residues and other conserved residues characteristic of Kunitz family members (FIG. 1B). SV-66 exhibited a basic arginine residue at position 15, which was the predicted P1 residue. This finding suggested that SV-66 may be an active protease inhibitor. In contrast, SV-170 had a threonine at the predicted P1 position, which suggested a lack of a canonical inhibitory activity against trypsin-like serine proteases, but which was similar to the C-terminal Kunitz domain of boophilin (Macedo-Ribeiro et al., 2008, *PLoS One;* 3:e1624).

Figure 2B:
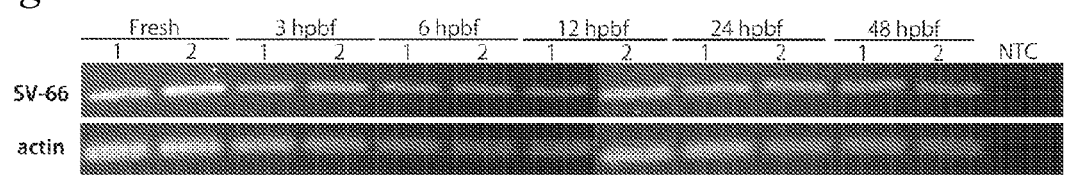
Figure 7:
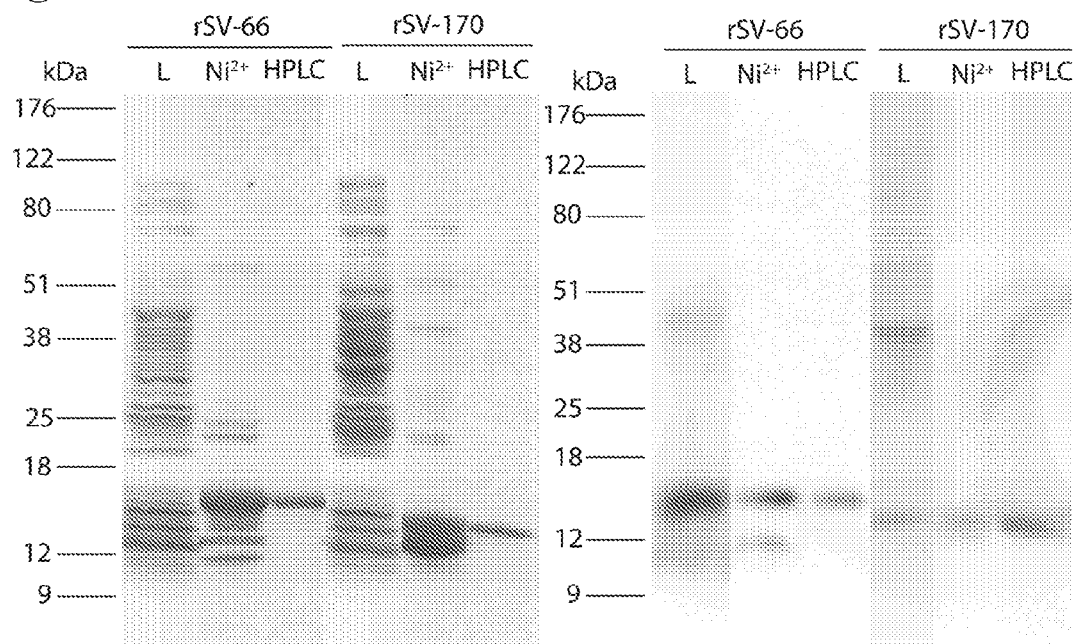
FIG. 7. Visualization of rSV-66 and rSV-170 following separation by SDS-PAGE (left panel) and immunoblotting (right panel). The SDS-PAGE gel was stained with Coomassie Brilliant Blue, while the immunoblot was probed with an anti-His primary antibody and visualized by chemiluminescence.

SV-66 is expressed in female salivary glands. RT-PCR assays were performed to qualitatively assess SV-66 expression in adult *S. vittatum*. Amplicons of expected size were detected in cDNA samples prepared from the female body (head and thorax) but not in female carcasses (female body minus salivary glands and head) or adult males (FIG. 2A). Time course studies indicated that SV-66 was expressed by adult females prior to blood feeding as well as at all time points sampled after blood feeding (FIG. 2B). Taken together, these results suggested that SV-66 was constitutively expressed in the salivary glands of adult females but was not expressed in males.

rSV-66 inhibits plasma clotting, while rSV-170 does not. SV-66 and SV-170 cDNAs were cloned into the pET-30 Ek/LIC vector (Novagen) and expressed each in *Escherichia coli* as recombinant (r) proteins with C-terminal double His tags. Two-step purification using $Ni^{2+}$ resin and RP-HPLC yielded fractions highly enriched for rSV-66 or rSV-170 (FIG. 7).

Figure 3:
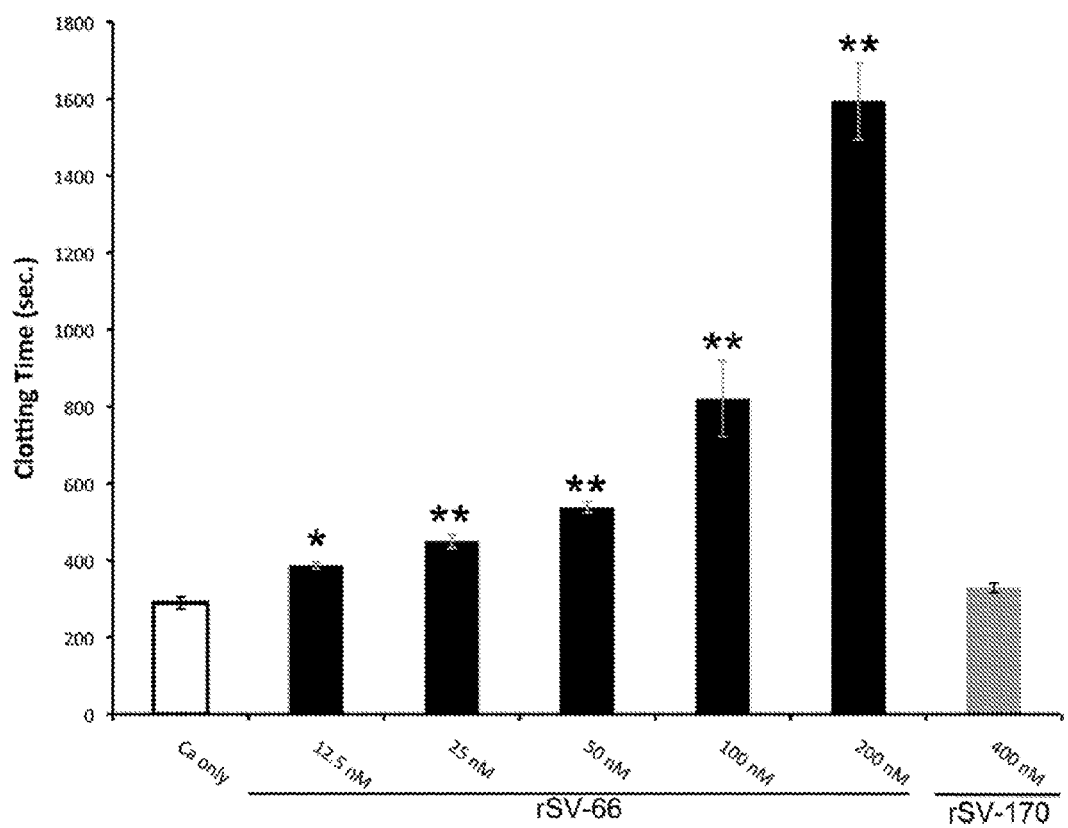
FIG. 3. rSV-66 delays clotting of human plasma. Indicated concentrations of rSimukunin (rSV-66) and rSV-170 were tested by the recalcification time assay. Citrated human plasma (50 µl) was mixed with recombinant proteins (in 50 µl 0.15 M NaCl, 10 mM HEPES pH7.4) and pre-warmed at 37° C. for 15 min before clotting was initiated by the addition of 50 µl prewarmed $CaCl_2$ (25 mM). Recalcification (clotting) time was determined by monitoring absorbance at 650 nm at 10-sec intervals in a SpectraMax 340 microtiter plate reader, with onset time (the time to a linear increase in the OD, which reflects the maximal rate of formation of insoluble fibrin) set at an OD of 0.04. Clotting times (mean±SD) for rSimukunin and rSV-170 are shown in black bars and grey bars, respectively. The white bar is the $Ca^{2+}$-only control. One-way analysis of variance indicted a significant difference between treatments ($F_{6,21}=119.3$; $P<0.001$) for rSimukunin but not rSV-170. Subsequent multiple comparisons between various treatments and the positive control were performed using the Holm-Sidak method. Statistically significant increases in clotting time at $p<0.05$ and $p<0.01$ are indicated by * and ** respectively. Results shown are representative of three independent experiments.

The effect of rSV-66 and rSV-170 on the time needed for fibrin deposition from $Ca^{2+}$-stimulated normal human plasma (clotting time) was determined by measuring the increase in OD at 650 nm. rSV-66 prolonged coagulation time in a dose-dependent manner, beginning at concentrations as low as 12.5 nM, whereas rSV-170 exhibited no anti-coagulation activity up to a concentration of 400 nM (FIG. 3). Since rSV-170 did not inhibit coagulation, the remainder of this example focused on rSV-66. Given its anticoagulant activity, rSV-66 was named "Simukunin", after a contraction of *Simulium kunitz* inhibitor. Recombinant Simukunin is also referred to herein as rSimukunin.

Figure 4:
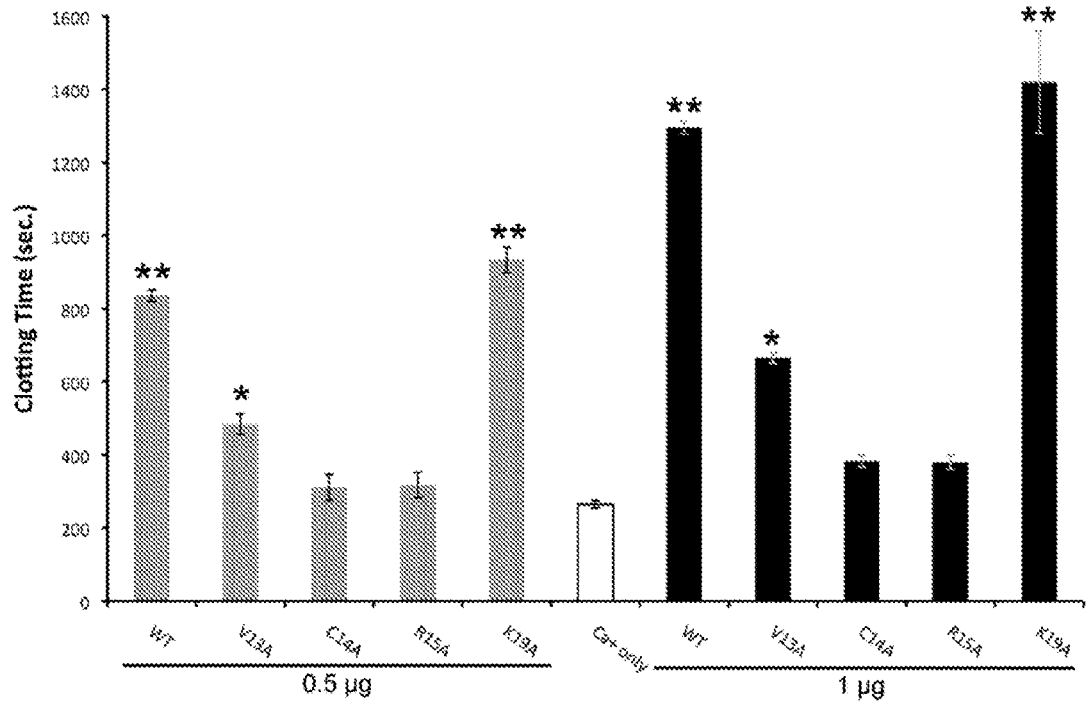
FIG. 4. Point mutations in the reactive site loop of rSimukunin disable anti-coagulation activity. Each recombinant protein was tested by adding 0.5 µg (grey bars) or 1 µg (black bars) to a fixed volume of plasma. Plasma was then pre-warmed at 37° C. for 15 min before addition of 25 mM (8.3 mM final concentration) $CaCl_2$ (pre-warmed) to initiate clotting. White bar shows the $Ca^{2+}$-only plasma control. The graph shows mean±SD from three independently conducted experiments. p-values for significant differences by one-tailed t-test are shown, where the alternative hypothesis is that sample recalcification time is greater than the $Ca^{2+}$-only control. Statistically significant increases in clotting time at $p<0.05$ and $p<0.01$ are indicated by * and ** respectively FIG. 5. rSimukunin inhibits several serine proteases. Enzyme activity in the presence of 500 nM of rSimukunin, as a percentage of the total activity in the absence of inhibitor, is shown. Results with statistically significant (t-test, $p<0.01$) inhibition compared to the control are shown in white bars. The graph shows mean±SEM. u-PA: urokinase-type plasminogen activator, t-PA: tissue plasminogen activator. Each inhibition assay was conducted in triplicate.
Figure 5:
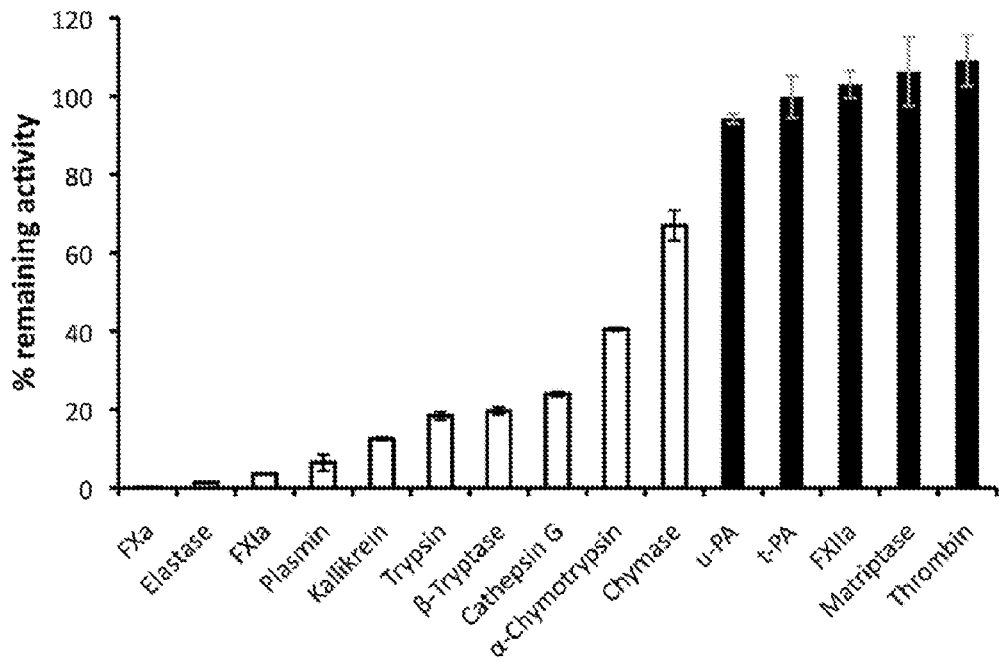

Residues in the reactive site loop are important for rSimukunin anti-coagulation activity. Since canonical Kunitz inhibitors interact with target proteases through their reactive site loop (RSL), whether alanine replacement of residues in or adjacent to the RSL affected Simukunin activity was addressed by producing three alanine replacement mutants, SV66V13A, SV66C14A, and SV66R15A. A fourth mutant, SV66K19A, was also produced as a control protein with an alteration outside of the RSL domain that should not affect anticoagulation activity. Following purification by $Ni^{2+}$ affinity resin and reversed-phase HPLC, it was observed that each recombinant protein ran as a doublet on SDS-PAGE gels. Tryptic digestion and mass spectrometry analysis, however, indicated that both bands consisted solely of Simukunin that were identical to full length native Simukunin. This analysis also indicated that the low molecular-weight band corresponded to loss of one of the epitope tags, possibly due to cleavage by an K coli protease during the lysis step. Thus, it was concluded that the presence of this lower band should not affect the RSL or activity. However, its presence necessitated the use of μg rather than molar concentrations in coagulation assays since precise calculation of molar concentrations was impossible. Therefore anticoagulation assays were conducted by adding 0.5 or 1.0 μg of WT or mutant rSimukunin to plasma and the rapidity of clotting compared to plasma without rSimukunin by pairwise t-test. The presence of WT rSimukunin significantly increased clotting time as did addition of SV66K19A. In contrast, the addition of SV66C14A and SV66R15A to plasma had no significant effect on clotting activity. SV66V13A delayed coagulation, but this effect was reduced compared to the delay produced by WT rSimukunin (FIG. 4).

rSimukunin inhibits activity of multiple proteases including coagulation factors. Preliminary assays indicated that rSimukunin also inhibited the enzymatic activity of enterokinase, which suggested rSimukunin could inhibit other serine proteases besides those with roles in host coagulation. The inhibitory activity of rSimukunin against 15 different serine proteases, including the coagulation factors FXa, FXIa, FXIIa, and thrombin, was characterized. Results indicated that rSimukunin significantly reduced the activity of ten of these proteases (FIG. 5). In the coagulation cascade, rSimukunin significantly inhibited FXa and FXIa, but not thrombin or FXIIa. Other enzymes strongly inhibited by rSimukunin were elastase, plasmin, kallikrein, trypsin, β-tryptase, and cathepsin G (FIG. 5).

The $IC_{50}$ of rSimukunin to the most strongly inhibited proteases was determined in order to assess the relative affinity of this inhibitor for each target (Table 1). To obtain linear reaction rates within the time frame of the experiment, each target enzyme was assayed at different molar concentrations. The molar ratio of rSimukunin to the enzyme at the $IC_{50}$ (Table 1) was also calculated. Collectively, the results indicated that rSimukunin most strongly inhibited elastase with an $IC_{50}$ of 4.9 nM and a ratio of inhibitor to enzyme of 27.22. Factor Xa was also strongly inhibited, with an $IC_{50}$ of 5.2 nM and a molar ratio of 52.00, as was cathepsin G with a molar ratio of 32.45. The other enzymes tested, including FXIa, required molar excesses of hundreds- to thousands-fold for 50% inhibition of proteolytic activity.

TABLE 1

IC50 values for rSimukunin against various serine proteases.

| Enzyme | Concentration (nM) | $IC_{50}$ (mean ± SEM (nM)) | Ratio |
|---|---|---|---|
| Elastase | 0.18 | 4.9 ± 0.6 | 27.22 |
| Cathepsin G | 6.7 | 217.4 ± 5.7 | 32.45 |
| Factor Xa | 0.1 | 5.2 ± 0.3 | 52.00 |
| Plasmin | 0.2 | 32.2 ± 5.2 | 161.00 |
| Factor XIa | 0.06 | 56.7 ± 13.1 | 945.00 |
| Kallikrein | 0.08 | 91.8 ± 6.3 | 1147.50 |
| Trypsin | 0.1 | 379.3 ± 30.2 | 3793.00 |
| β-Tryptase | 0.01 | 66.8 ± 14.6 | 6680.00 |

Figure 8:
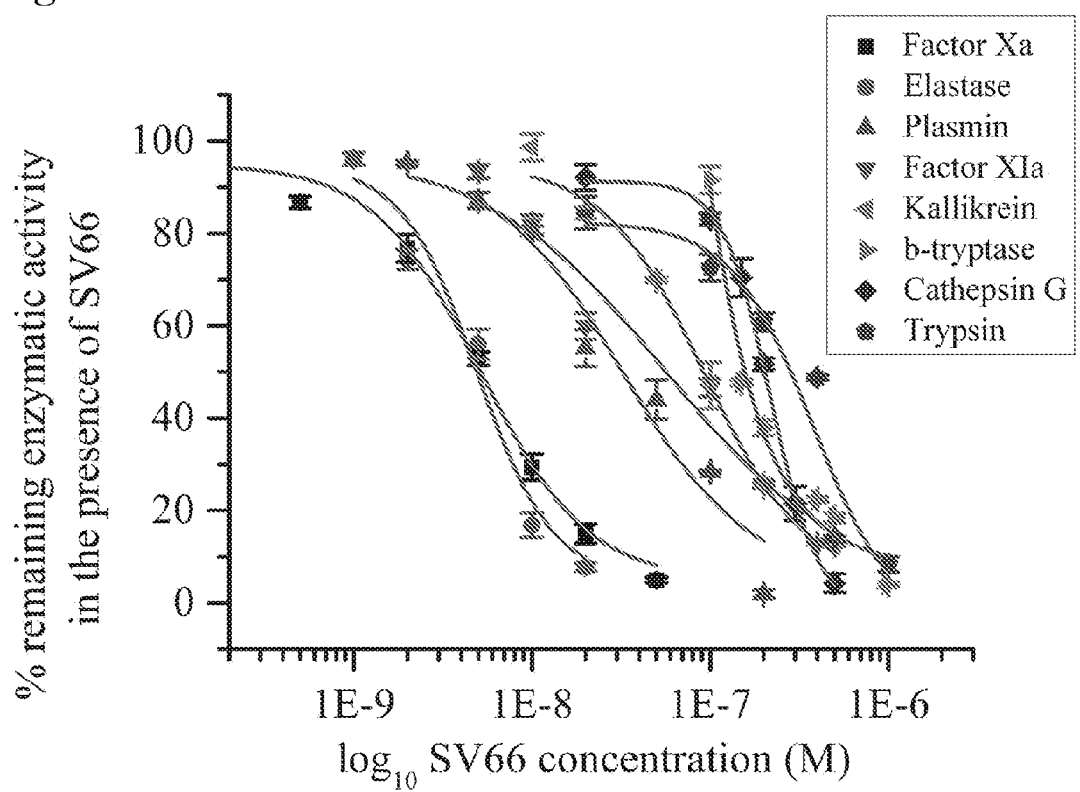
FIG. 8. Determination of rSimukunin $IC_{50}$ values for selected serine proteinases.

Titrated concentrations of rSimukunin were tested with constant concentrations of enzymes (in Concentration column) to determine the concentrations of rSimukunin that gave a 50% inhibition of the enzyme activity. Ratios of $IC_{50}$ to enzyme concentration are also shown as different concentrations of enzymes were necessary to obtain linear reaction rates. Titration curves are shown in FIG. 8.

Figure 6A:
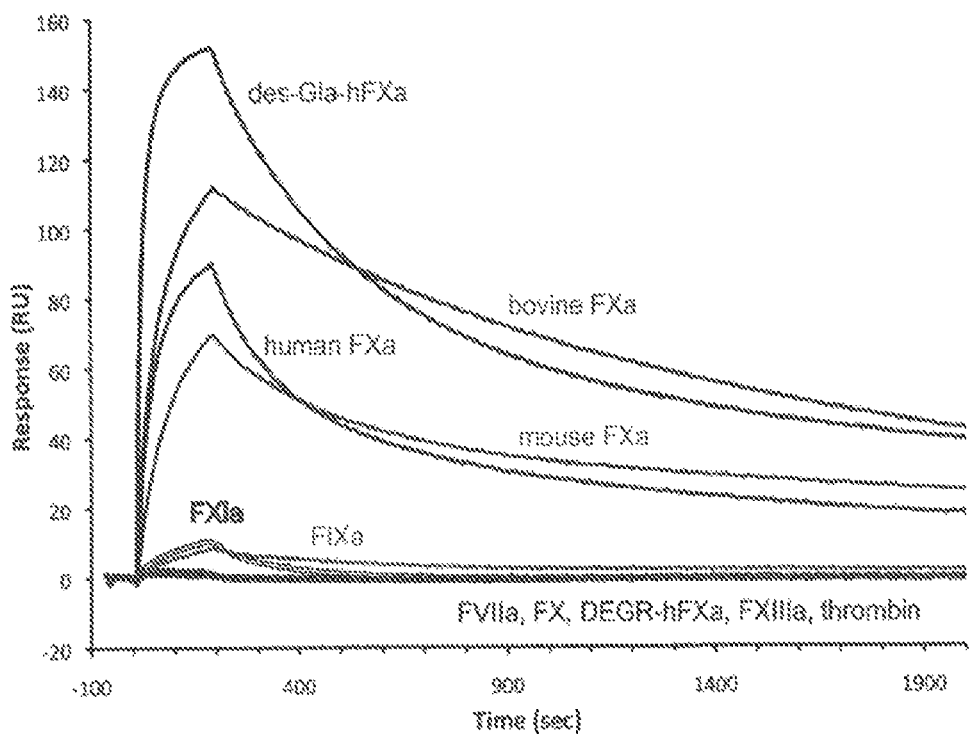
Figure 6B:
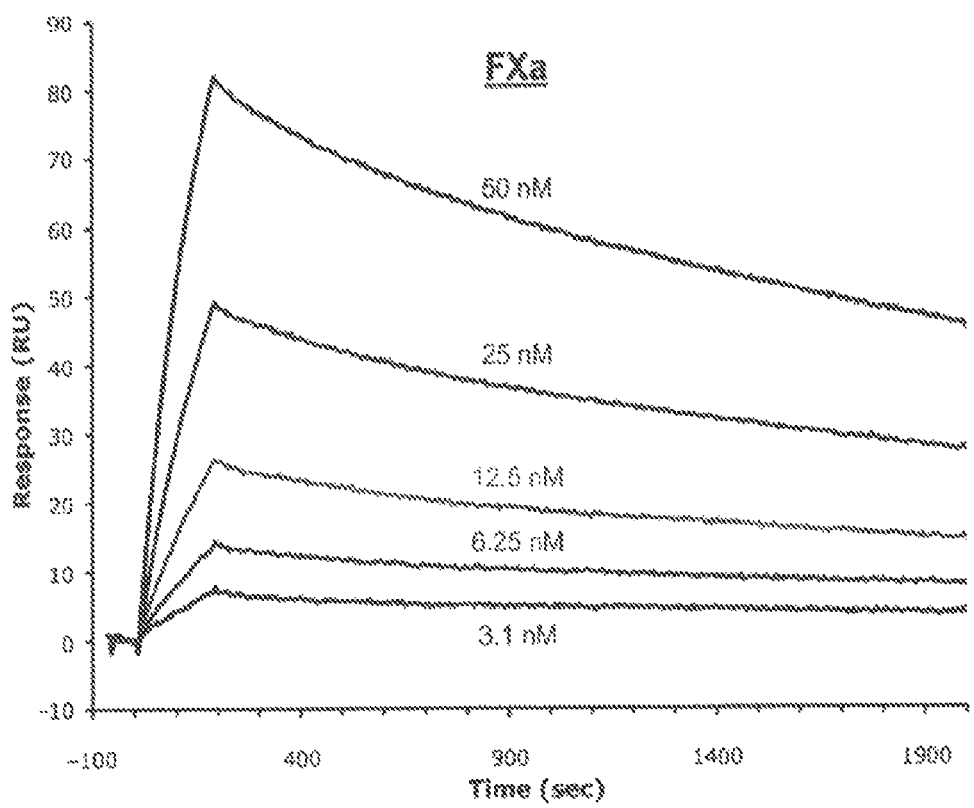

As elastase, FXa, and cathepsin G were the most strongly inhibited, based on the ratio of inhibitor to enzyme (Table 1), the $K_m$ for these three enzymes was determined, and then used the approach of Cheng and Prusoff (Cheng and Prusoff, 1973, *Biochem Pharmacol;* 22:3099-3108) to calculate the $K_i$ from the IC50, with a final substrate concentration of 250 uM. The $K_m$ for the elastase substrate was 38.5±3.3 μM, and the estimated $K_i$ was ~0.65 nM. For FXa the substrate $K_m$ was 161.6±17.4 μM, and the estimated $K_i$ was ~2.1 nM. For Cathepsin G the $K_m$ was 188±20 μM, and the $K_i$ was 100 nM. A general chymotrypsin substrate was used to assess Cathepsin G activity; as this substrate is not optimized for Cathepsin G it is likely that our measurement of the $K_i$ underestimates the effect of rSimukunin. Further studies of the effect of rSimukunin on Cathepsin G will be performed.

rSimukunin displays high affinity binding to FXa and elastase. The preceding results provided measures of affinity for elastase, FXa, and cathepsin G by rSimukinun, but were insufficient for calculation of binding and dissociation kinetics. Therefore, Surface Plasmon Resonance (SPR) studies were conducted using rSimukunin immobilized on a sensor chip and used selected target enzymes as the analyte. These studies showed that rSimukunin bound FXa from several mammals (human, mouse and bovine) with high affinity (FIG. 6A). rSimukunin also bound DES-Gla-FXa, an FXa derivative lacking the Gla domain necessary for docking onto a negatively charged membrane surface. In contrast, rSimukunin did not bind DEGR-FXa, a derivative blocked at the active site, or FX, which is the zymogen precursor of FXa (FIG. 6A). rSimukunin also exhibited very weak binding responses to FIXa and FXIa, and no binding responses to FVIIa, FXIIIa or thrombin (FIG. 6A). Kinetic analysis determined that FXa bound rSimukunin with a $K_D$ of 3.07 nM (FIG. 6B and Table 2), but assays with elastase revealed an even stronger affinity for rSimukunin with a $K_D$=~0.4 nM (FIG. 6C and Table 2). These $K_D$ values are consistent with the $K_i$ values we calculated based on the $K_m$ and $IC_{50}$. The low $K_D$ values for both FXa and elastase result from a fast association rate (ka1=4.3 $10^7$ $M^{-1}s^{-1}$ for elastase) and a very slow off rate (kd1=0.017 $s^{-1}$) indicative of rSimukunin functioning as a tight-binding inhibitor.

TABLE 2

Kinetics of FXa and Elastase interactions with rSimukunin.

| Enzyme | ka1($M^{-1}s^{-1}$) | kd1($s^{-1}$) | $K_D$(nM) |
|---|---|---|---|
| FXa | 9.87 $10^4$ | 3.032 $10^{-4}$ | 3.071 |
| Elastase | 4.302 $10^7$ | 0.01727 | 0.40 |

Responses were obtained by injecting FXa or elastase over immobilized rSimukunin for 180 seconds at a flow rate of 30 μl/minute. Data were derived from Ka1 and Kd1 and fitted using the Langmuir (1 1 binding) equation. Kinetic values obtained from the sensorgrams presented in FIGS. 6B and 6C for FXa and elastase respectively.

Discussion

Salivary gland extracts from *S. vittatum* have long been known to have potent anticoagulant activity, but the identity of the molecules involved had heretofore remained uncharacterized. This Example demonstrates that of the two Kunitz family proteins expressed in the salivary glands of female *S. vittatum* (Andersen et al., 2009, *J Proteome Res;* 8(3):1474-1488), rSV-66, which was named Simukunin, dose-dependently prolongs coagulation times of human plasma while rSV-170 lacks anticoagulant activity. Simukunin is constitutively expressed specifically in adult female salivary glands, which is consistent with a role in blood feeding.

SPR results strongly suggest that the anticoagulant activity of Simukunin is primarily due to high affinity binding to FXa. In contrast, rSimukinin does not bind to the zymogenic form of FX, which suggests this inhibitor only interacts with the activated enzyme. Results further show that rSimukunin exhibits binding to des-Gla-FXa but does not interact with DEGR-FXa, which is blocked specifically at the active site. These data together with outcomes of the mutagenesis studies strongly suggest that rSimukunin interacts directly with the active site of FXa. That FXa is a primary target of rSimukunin is also supported by results showing that rSimukunin does not interact with FVIIa, FXIIa, FXIIIa, or thrombin, and only weakly interacts with FIXa and FXIa.

The loss of anticoagulation activity by SV66R15A indicates that rSimukunin interacts directly with the active site of FXa, and that Arg15 functions as the P1 residue. The reduced activity of SV66V13A could likewise reflect a less stable interaction with the catalytic active site of FXa, while the lack of activity of SV66C14A likely reflects an alteration in structure due to elimination of the Cys14-Cys38 disulfide bond. Taken together, the data indicate that Simukunin acts similarly to BPTI, whose basic P1 residue, Lys15, is critical for the inhibition of trypsin and chymotrypsin (Tschesche et al., 1987, *Biochim Biophys Acta;* 913:97-101) through stable docking into the S1 specificity subsite of these enzymes and formation of polar interactions with a negatively charged Asp189 side chain (Ascenzi et al., 2003, *Curr Protein Pept Sci;* 4:231-251).

The anti-clotting activity of Simukunin may account for the anti-FXa activity of black fly SGE described previously (Jacobs et al., 1990, *Thromb Haemost;* 64:235-238). However, the estimated size of a partially characterized FXa inhibitor was 18000 Da (Jacobs et al., 1990, *Thromb Haemost;* 64:235-238), which is much larger than the predicted size of Simukunin (9627.22 Da). Although Simukunin has a putative O-glycosylation site in the C-terminal region, the 1D SDS-PAGE gel band from which Simukunin tryptic fragments were recovered migrated between the 14.1 and 6 kDa markers in Andersen et al. (Andersen et al., 2009, *J Proteome Res;* 8(3):1474-1488), which indicates that glycosylation does not significantly add to the native size of Simukunin. The relationship between Simukunin and the previously described anti-FXa activity thus remains unclear but it is possible that other proteins contribute to the anti-FXa activity in black fly saliva.

Although rSimukunin inhibited kallikrien, the activity was modest, and further, it did not inhibit bradykinin production from kaolin-activated human plasma, indicating that the FXII/prekallidrein/kallikrein pathway is not a target of this inhibitor.

Coagulation and inflammation are linked through a variety of cross-talk mechanisms (Levi and van der Poll, 2010, *Grit Care Med;* 38:S26-34). For example, proteinase-activated receptor 4, which is highly expressed on platelets, is activated following cleavage by FXa or thrombin and subsequently mediates inflammatory responses (Levi and van der Poll, 2010, *Grit Care Med;* 38:S26-34; and McDougall et al., 2009, *Arthritis Rheum;* 60:728-737). As Simukunin inhibits FXa, which indirectly reduces subsequent thrombin activation, it is likely that Simukunin may also influence inflammatory responses at the bite site, though we have not yet examined this experimentally.

The comparative data of this example clearly show that rSimukunin binds to and/or inhibits several other enzymes besides FXa including major components of neutrophil azurophil granules such as elastase, and mast cell proteases including cathepsin G, tryptase, and chymase. Indeed, the strongest binding affinity we detected was between rSimukunin and elastase. This finding together with inhibition of cathepsin G is notable because both enzymes function in killing phagocytized microbes by neutrophils. Extracellular release of cathepsin G mediates platelet aggregation, which is known to provide a surface for assembly of the prothrombinase complex (Levi and van der Poll, 2010, *Crit Care Med;* 38:S26-34). Thus, inhibition of cathepsin G could indirectly antagonize coagulation. Cathepsin G, tryptase, and elastase also regulate the function of several chemokines, cytokines, cell surface receptors and adhesion molecules (Pham, 2006, *Nat Rev Immunol;* 6:541-550; Pham, 2008, *Int J Biochem Cell Biol;* 40:1317-1333; Trivedi and Caughey, 2010, *Am J Respir Cell Mol Biol;* 42:257-267; and Zhao et al., 2005, *J Immunol;* 175:2635-2642), which leads to the possibility that Simukunin may affect inflammation or other responses in proximity to sites of black fly feeding. Further experimental work will be necessary to examine the effect of Simukunin on macrophage, mast cell, and neutrophil function.

The inhibition of elastase by rSimukunin is somewhat surprising in light of prior studies showing that Kunitz domain inhibitors of elastase like Bikunin (formerly called acid stable trypsin inhibitor or ASTI, or urinary trypsin inhibitor) have an aliphatic amino acid, such as methionine, leucine, or valine in the P1 position (Fries and Blom, 2000, *Int J Biochem Cell Biol;* 32:125-137; Albrecht et al., 1983, *Hoppe Seylers Z Physiol Chem;* 364:1697-1702; Albrecht et al., 1983, *Hoppe Seylers Z Physiol Chem;* 364:1703-1708; and Tschesche and Wenzel, 1983, *Adv Exp Med Biol;* 156:329-337). Thus, it is likely that residues outside the RSL either orient the Simukunin/elastase interaction to permit tight binding despite the unfavorable P1 residue, or that binding and inhibition involves interactions with a domain distinct from the RSL. Further structure-function experiments will address how Simukunin interacts with this enzymatic target.

Inhibition of multiple enzymes by rSimukunin, is also not unusual for Kunitz family inhibitors from blood-feeding arthropods and other organisms. For example, the archetypical Kunitz protein BPTI inhibits trypsin with a $K_i$ of 0.06 pM, but it also inhibits chymotrypsin ($K_i$=9 nM), plasmin, and kallikrein (Vincent and Lazdunski, 1973, *Eur J Biochem;* 38:365-372). Boophilin, a tick salivary protein with two Kunitz domains, likewise exhibits significant inhibitory activity toward thrombin, trypsin, plasmin, and plasma kallikrein (Macedo-Ribeiro et al., 2008, *PLoS One;* 3:e1624), while the serpin IRS-2 has inhibitory activity against cathepsin G, chymase, and a-chymotrypsin (Chmelar et al., 2011, *Blood;* 117:736-744). On the other hand, Kunitz family thrombin inhibitors from soft ticks appear to specifically inhibit thrombin at pM concentrations (eg. ornithodorin, $K_i$=1 pM (van de Locht et al., 1996, *EMBO J;* 15:6011-6017); savignin, $K_i$=4.89 pM) (Nienaber et al., 1999, *Exp Parasitol;* 93:82-91). Lastly, it is noted that the binding affinities of Simukunin for FXa ($K_D$=3.071 nM) and elastase ($K_D$=0.4 nM) are broadly consistent with the binding affinities determined for other Kunitz inhibitors from blood feeding species. As examples, the tick salivary inhibitor ixolaris binds to FX and FXa with $K_D$s of 0.67 and 0.25 nM respectively (Monteiro et al., 2008, *Protein Sci;* 17:146-153), while boophilin binds thrombin with a $K_i$ of 1.8 nM (Macedo-Ribeiro et al., 2008, *PLoS One;* 3:e1624), as does amblin, with a $K_i$ of 20 nM (Lai et al., 2004, *Gene;* 342:243-249).

Future functional studies will more fully characterize the role of Simukunin in blood feeding. Nonetheless, the results of this example collectively suggest Simukunin facilitates blood-feeding by disrupting coagulation and possibly by interfering with host inflammatory responses. Several examples from mosquitoes and sandflies also implicate saliva in potentiating pathogen transmission by modulating immune responses in the host skin (reviewed in Schneider and Higgs, 2008, *Trans R Soc Trop Med Hyg,* 102:400-408; Titus and Ribeiro, 1988, *Science;* 239:1306-1308; and Oliveira et al., 2008, *PLoS Negl Trop Dis;* 2:e226). However, future studies will be required to determine whether Simukunin affects pathogen transmission by black flies. Lastly, recent studies of the sialome from another black fly, *Simulium nigrimanum*, identified four Kunitz protein-encoding transcripts, which are divided into two subfamilies based on the presence or absence of a C-terminal extension of basic residues (Ribeiro et al., 2010, *Am J Trop Med Hyg,* 82:1060-1075). Therefore, *S. nigrimanum* salivary glands may also produce multiple Kunitz anti-coagulation factors with potential roles in regulating coagulation and inflammation.

Materials and Methods

*S. vittatum* culture. *S. vittatum* was reared at the Department of Entomology, the University of Georgia, according to previously described conditions (Gray E W, Noblet R. Laboratory Rearing of Black Flies. In: Maramorosch K, Mahmood F, editors. Maintenance of Human, Animal and Plant Pathogen Vectors. New Delhi and Calcutta: Oxford & IBH Publishing Co. PVT. LTD; 1999; and Bernardo and Cupp, 1986, *J Med Entomol;* 23:666-679). Because *S. vittatum* is facultatively autogenous, no vertebrate animals were used in the study for rearing or maintenance of insects.

Salivary gland dissection, cDNA synthesis, and expression analyses. Adult female flies (collected 2-3 days post eclosion) were chilled on ice, and their salivary glands were collected by dissection under a stereomicroscope in sterile HEPES saline (HS) (10 mM HEPES pH 7.0, 150 mM NaCl). Fifty salivary gland pairs were collected in 20 µL HS, mixed with 20 µL RNAlater® (Ambion, Foster City, Calif.), and stored at −70° C. until use. Total RNA was isolated using Trizol reagent (Invitrogen, Carlsbad, Calif.). Genomic DNA was removed using RNase-free DNase (Turbo DNase, Ambion, Foster City, Calif.). First strand cDNA was synthesized using 100 ng of total RNA, SuperScript III (Invitrogen, Carlsbad, Calif.) and an oligo d(T) primer (5'-(T)$_{25}$-VN-3') at 50° C. for 60 min, followed by enzyme inactivation at 70° C. for 15 min. Resultant cDNA was then stored at −20° C. until use.

Total RNA was isolated and reverse transcribed as described above from female flies without salivary glands and head (termed "carcass"), intact female flies, and intact males flies. Since *S. vittatum* is autogenous for the first gonotrophic cycle, reverse transcribed RNA from female bodies without abdomens was also used (in order to avoid collecting vertebrate cells in the blood meal) collected after the first oviposition, and at 3, 6, 12, 24, and 48 hrs post blood-feeding (pbf). Blood-fed flies were kept at 27° C. with constant access to sugar water (10% sucrose). RT-PCRs were then run using an Eppendorf thermocycler in 25 µl reaction volumes containing 1 µl of cDNA and 2.5 µM of SV-66 UA and SV-66 DA primers. Primers are shown in Table 3. Cycling conditions were as follows: initial 2 min denaturation at 94° C., followed by 30 cycles at 30 sec at 94° C., 30 sec at 57° C. 30 sec at 72° C., and a final 5 min extension at 72° C. Actin from *S. vittatum* (GenBank accession number AY083375.1) amplified using SVactinUA and SVactinDA primers was used as an endogenous control.

The PCR primers used in this example are shown in Table 3. For primers used for cloning in pET-30, direction-specific LIC sites are shown in italics. For primers used for single His-tag constructs, bold letters indicate the stop codon (TAA) and the read-through Ala (GCA in reverse-complement orientation).

TABLE 3

Primers

| Primer | Sequence (5' → 3') | SEQ ID NO |
|---|---|---|
| SvactinUA | TGTGTTACGTTGCCTTGGACTTTG | 17 |
| SvactinDA | TGATGGAGTTGTAGACGGTTTCGTG | 18 |
| SV66UA | TGAATTGGATCGAAATGAATATACTTCCA | 19 |
| SV66DA | TTAGTTTGAATGTCCTTTTTAGTCCAACGA | 20 |
| SV170UA | CACCTGAGAGAATCTTCTGCGTCAAA | 21 |
| SV170DA | CGGTCAATACATTTTTATCCTCTTGTGCT | 22 |
| SV66UB | GACGACGACAAGATGCAAGAGAACGTTTGCAATCTTC | 23 |
| SV66DB | GAGGAGAAGCCCGGTTAGTCCAACGAAATAATTGGTATC | 24 |
| SV66DC | GAGGAGAAGCCCGGTGCGTCCAACGAAATAATTGGTATCG | 25 |
| SV170UB | GACGACGACAAGATGAAGTCAGCTGACATCTGCAGA | 26 |
| SV170DB | GAGGAGAAGCCCGGTTACATACACTTGGCTTTACATTCT | 27 |
| SV170DC | GAGGAGAAGCCCGGTGCCATACACTTGGCTTTACATTCTTG | 28 |
| V13A-UA | CCGGTGGACGAAGGTGCATGTAGAGCGTTATTC | 29 |
| V13A-DA | GAATAACGCTCTACATGCACCTTCGTCCACCGG | 30 |
| C14A-UA | AATCTTCCGGTGGACGAAGGTGTAGCTAGAGCGTTATTCA | 31 |
| C14A-DA | TGAATAACGCTCTAGCTACACCTTCGTCCACCGGAAGATT | 32 |
| R15A-UA | CTTCCGGTGGACGAAGGTGTATGTGCAGCGTTATTCAAGC | 33 |
| R15A-DA | GCTTGAATAACGCTGCACATACACCTTCGTCCACCGGAAG | 34 |
| K19A-UA | GGTGTATGTAGAGCGTTATTCGCGCGTTTTTACTACGAACCC | 35 |
| K19A-DA | GGGTTCGTAGTAAAAACGCGCGAATAACGCTCTACATACACC | 36 |

Cloning and sequence analysis of Kunitz family proteins. Full-length cDNAs for SV-66 and SV-170 (GenBank accession numbers EU930300 and EU930227, respectively) (Andersen et al., 2009, *J Proteome Res;* 8(3):1474-1488) were amplified from salivary gland cDNA using Platinum HIFI Taq DNA polymerase and gene specific primers (SV66 UA, SV66DA, SV170UA, SV170DA) in 25 µl reactions. PCR conditions were: initial 2 min denaturation at 94° C., followed by 35 cycles (30 sec at 94° C., 30 sec at 57° C. 30 sec at 68° C.), and a final 5 min extension at 68° C. The resulting amplicons were then TA cloned into pCR4-TOPO (Invitrogen), and transformed into *E. coli* TOP10 competent cells (Invitrogen). After overnight culture, the plasmids SV66/TOPO and SV170/TOPO were purified using the Wizard Plus miniprep DNA purification system (Promega, Madison, Wis.) and quantified using a NanoDrop spectrophotometer (Thermo Scientific, Wilmington, Del.). Inserts were sequenced (Macrogen, Rockville, Md.) to confirm fidelity with the reference sequences. SignalP (Emanuelsson et al., 2007, *Nat Protoc;* 2:953-971) was used to predict signal peptide sequences, and NetOGlyc (Julenius et al., 2005, *Glycobiology;* 15:153-164) was used to predict potential glycosylation sites. Alignments were performed using Clustal W2 (Larkin et al., 2007, *Bioinformatics;* 23:2947-2948) against other Kunitz domains from the following Kunitz inhibitors: bovine pancreatic trypsin inhibitor (BPTI) (Genbank accession number AAI49369) from *Bos taurus* (a single Kunitz domain inhibitor); human tissue factor pathway inhibitor (TFPI) (P10646) (consisting of 3 Kunitz domains); a thrombin inhibitor, amblin, (AAR97367) from the tick *Amblyomma hebraeum* (2 Kunitz domains); and a prothrombinase inhibitor, boophilin, (CAC82583) from the tick *Rhipicephalus* (*Boophilus*) *microplus* (2 Kunitz domains).

Protein expression and purification. For bacterial expression of SV-66 and SV-170, full-length ORFs without signal peptides were PCR amplified using SV66/TOPO or SV170/TOPO as template, the primers SV66UB/SV66 DB or SV170UB/SV170 DB (Table 3), and Elongase polymerase enzyme mix (Invitrogen). The resulting products were then directly cloned in frame with the C-terminal His-tag of the vector pET-30 (Novagen) using T4 polymerase. Mutants SV66V13A, SV66C14A, SV66R15A, and SV66K19A were generated using the Quick Change site-directed mutagenesis kit (Strategene) together with the primers V13A-UA/V13A-DA, C14A-UA/C14A-DA, R15A-UA/R15A-DA, and K19A-UA/K19A-DA respectively. Each of these constructs were confirmed by DNA sequencing, and then expressed by transforming into *E. coli* BL21 (DE3) cells cultured in SOC medium (0.5% Yeast Extract, 2% Tryptone, 10 mM NaCl, 2.5 mM KCl, 10 mM $MgCl_2$, 10 mM $MgSO_4$, 20 mM Glucose), supplemented with 10 ug/ml of kanamycin to an O.D. of 1.0 at 37° C. 0.1 mM isopropyl-β-d-thiogalactopyranoside (IPTG) was then added to the cultures and grew an additional 17-24 h at 20° C. Bacterial cells were harvested by centrifugation at 4500 g for 10 min and used immediately or stored at −80° C.

Bacterial pellets from 0.8 L cultures were resuspended in 40 ml of lysis buffer (50 mM Tris-HCl pH 8.0, 300 mM NaCl, 10 mM imidazole). After addition of lysozme (1 mg/ml) in 50 mM Tris-HCl (pH 8.0), cells were incubated on ice for one hour followed by two freeze-thaw cycles and sonication with six, 10 sec bursts at 300 W using a Branson 450 Sonifier (VWR). The lysate was then centrifuged at 13,000 g for 10 min, followed by 3 h incubation of the supernatant with Ni-NTA Superflow beads (Qiagen) pre-equilibrated with lysis buffer. After washing, attached proteins were eluted with three column volumes of elution buffer (50 mM Tris-HCl pH 8.0, 300 mM NaCl, 300 mM imidazole), followed by desalting and concentration using an Amicon Ultra-4 3000 MWCO spin column (Millipore, USA). Proteins were quantified using the Micro BCA Protein Assay Kit (Pierce) and visualized after SDS-polyacrylamide gel electrophoresis (PAGE) (4-20% precast gels (Lonza)) by staining with Coomassie Blue.

Recombinant proteins were further purified by reversed-phase high-performance liquid chromatography (RP-HPLC) using a Jupiter C4 column (5 μm particle size, 300 Å pore size, 250 mm length 2.00 mm ID) (Phenomenex, Torrance, Calif.) with a linear gradient between 95% H2O/5% acetonitrile (ACN)/0.05% trifluoroacetic acid (TFA)) and 95% ACN/ 5% H2O/0.03% TFA) monitored at 220 nm. Fractions were collected every minute, lyophilized to remove ACN and TFA, resuspended in 20 mM Tris pH 8.0, and quantified by the BCA method described above. Purity of the proteins was assessed by SDS-PAGE, performed as described above, and immunoblotting. Separated proteins were transferred onto a polyvinylidene fluoride (PVDF) membrane (Bio Rad, Hercules, Calif.), blocked in 1 PBS containing 0.05% Tween-20 and 2% non-fat skim milk for 1 hour at room temperature, and incubated with an anti-His primary antibody (His-probe (H-15); Santa Cruz Biotechnology) (15000). The membrane was washed three times with 1 PBS containing 0.05% Tween-20, incubated with goat anti-rabbit secondary antibody conjugated to horseradish peroxidase (Jackson Immuno Research) (110000), and visualized by chemiluminescence using the ECL Plus Western Blotting system (GE Healthcare, Piscataway, N.J.).

Recalcification assay. Recalcification assays were performed as described by Valenzuela et al. (Valenzuela et al., 1996, *Exp Parasitol;* 83:184-190). Briefly, 10 μL of various concentrations of recombinant proteins, 40 μL of 0.15 M NaCl, 10 mM HEPES pH7.4 and 50 μL of citrated human plasma (TriniCHECK™ Level 1, Trinity Biotech, Co Wicklow, Ireland) were mixed in a flat-bottomed 96-well plate and prewarmed at 37° C. for 15 min. To initiate plasma clotting, 50 μL of 25 mM $CaCl_2$ prewarmed to 37° C. was added in the 96-well plate. Immediately after the addition of $CaCl_2$ absorbance was taken at 650 nm at 10-sec intervals by microtiter plate reader at 37° C. (SpectraMax 340, Molecular Devices, Sunnyvale, Calif.). Clotting onset time ("Clotting Time") was set at the time when the absorbance reached an optical density (OD) of 0.04, where the increase in OD is linear. One-way ANOVA, followed by pairwise comparisons of treatment values to the $CaCl_2$-only control using the Holm-Sidak method, was used for the statistical analysis; when $p<0.05$, the difference was considered as statistically significant.

Serine protease inhibition assays. rSimukunin (500 nM) was first pre-incubated with each enzyme for 10 min before the addition of the corresponding substrate. The amount of enzyme used in the assays was the lowest possible to give a linear substrate hydrolysis rate in the assays ($r^2>0.95$). After incubation for 5 min at 30° C., substrate hydrolysis rate was followed in a Tecan Infinite M200 96-well plate fluorescence reader (Tecan group Ltd, Switzerland) using 365 nm excitation and 450 nm emission wavelength with a cutoff at 435 nm for 20 min at 30° C. Wells without enzyme were used to monitor spontaneous substrate hydrolysis and protease contamination in the inhibitor preparation. A t-test was used for the statistical analysis of the observed inhibition in the presence of 500 nM rSimukunin and when $p<0.05$, it was considered as statistically significant.

$IC_{50}$ estimates were determined as previously described (Kotsyfakis et al., 2007, *J Biol Chem;* 282:29256-29263), using decreasing concentrations of rSimukunin pre-incubated for 5 min with a given target enzyme, followed by addition of substrate. All experiments were performed in triplicate (for each enzyme and each concentration of the inhibitor). The mean percentage of enzymatic activity in the presence of various rSimukunin concentrations was then compared with enzymatic activity in the absence of rSimukunin. The sigmoidal fit of the data then yielded the estimate for the $IC_{50}$ of rSimukunin for the various enzymes. The resulting titration curves are provided in FIG. 8.

All enzymes used were of human origin and of the highest available purity. The source and concentration of the enzymes used in the serine protease screen assays follows: Thrombin (0.02 nM), a-chymotrypsin (0.025 nM), plasmin (0.2 nM) and chymase (1.8 nM) were purchased from Sigma (St. Louis, Mo.), skin β-tryptase (0.01 nM) was purchased from Promega (Madison, Wis.), activated coagulation factor X (FXa) (0.1 nM) was purchased from EMD Biosciences (La Jolla, Calif.), FXIIa (0.1 nM) was purchased from Haematologic Technologies Inc. (Essex Junction, Vt.), kallikrein (0.08 nM) was purchased from Fitzgerald Industries International (Concord, Mass.), elastase (0.18 nM) was purchased from Elastin Products (Owensville, Mo.), FXIa (0.06 nM), urokinase-type plasminogen activator (u-PA) (0.5 nM) and tissue plasminogen activator (t-PA) (0.06 nM) from Molecular Innovations (Southfield, Mich.), matriptase (0.2 nM) from R&D Systems (Minneapolis, Minn.), cathepsin G (6.7 nM) from Enzo Life Sciences (Plymouth Meeting, Pa.) and sequencing grade trypsin (0.1 nM) was purchased from Roche (Chicago, Ill.). The amount of enzyme used in each of the IC50 estimation assays is shown also in the Table 1.

Assay buffer for elastase and chymase was 50 mM HEPES buffer pH 7.4, 100 mM NaCl, and 0.01% Triton X-100. Assay buffer for trypsin, a-chymotrypsin, factor Ma, factor XIIa and thrombin was 50 mM Tris buffer pH 8.0, 150 mM NaCl, 20 mM $CaCl2$, and 0.01% Triton X-100. Assay buffer for β-tryptase was 50 mM Tris pH 8.0, 50 mM NaCl, and 0.05% Triton X-100. Assay buffer for kallikrein, matriptase and plasmin was 20 mM Tris buffer pH 8.5, 150 mM NaCl, and 0.02% triton X-100. Assay buffer for factor Xa was 20 mM Tris buffer pH 8.0, 200 mM NaCl, 5 mM CaCl2, and 0.1% BSA. Assay buffer for u-PA and t-PA was 20 mM Tris buffer pH 8.5, and 0.05% Triton X-100. Assay buffer for cathepsin G was 50 mM Tris buffer pH 7.4, 150 mM NaCl, and 0.01% Triton X-100. Peptidyl substrates used were: Suc-A-A-P-V-AMC for elastase, a-chymotrypsin and chymase (EMD Biosciences, La Jolla, Calif.); Boc-D-P-R-AMC for thrombin and plasmin; Boc-Q-A-R-AMC for trypsin, factor XIa and u-PA (Sigma, St. Louis, Mo.); Boc-F—S—R-AMC for β-tryptase; Suc-L-L-V-Y-AMC for chymase (Bachem, King of Prussia, Pa.); and methylsulfonyl-D-cyclohexylalanyl-G-R-AMC acetate for factor Xa, factor XIIa, t-PA, matriptase and kallikrein (American Diagnostica Inc., Stamford, Conn.). All substrates were used at 250 μM final concentration in all the assays.

Surface plasmon resonance (SPR) assays. SPR experiments were conducted using a T100 instrument (Biacore Inc., Uppsala, Sweden) following the manufacturer's instructions. Sensor CM5, amine coupling reagents, and buffers were also purchased from Biacore Inc. (Piscataway, N.J., USA). IBS P (10 mM Hepes, pH 7.4, 150 mM NaCl, and 0.005% (v/v) P20 surfactant) was used as the running buffer for all SPR experiments, which were carried out as previously described (Albrecht et al., 1983, *Hoppe Seylers Z Physiol Chem;* 364:1697-1702). For analytes, FVIIa (recombinant) was purchased from American Diagnostica (Stamford, Conn.); FX, FXa (human, bovine, mouse), DEGR-FXa (human), des-Gla-FXa (human), FIXa, FXIa, FXIIIa, and thrombin were purchased from Haematologic Technologies, Inc. (Essex Junction, Vt.); elastase (purified from human sputum) was purchased from Molecular Innovations, Inc. (Novi, Mich.). All enzymes were of the highest available purity. For immobilization and kinetic analysis, rSimukunin (10 μg/ml) in acetate buffer pH 5.0 was immobilized over a CM5 sensor via amine coupling, resulting in a final immobilization of 475.3 RU. Kinetic experiments were carried out with a contact time of 180 seconds at a flow rate of 30 μl/minute at 25° C. rSimukunin-FXa complex dissociation was monitored for 1800 seconds, and the sensor surface was regenerated by a pulse of 30 seconds of 20 mM HCl at 30 μl/minute. In other experiments, other coagulation factors or enzymes were used as analytes. Blank flow cells were used to subtract the buffer effect on sensorgrams. After subtraction of the contribution of bulk refractive index and nonspecific interactions with the CM5 chip surface, the individual association ($k_a$) and dissociation ($k_d$) rate constants were obtained by global fitting of data to a 11 interaction model (Langmuir) using BIAevaluation™ (Biacore, Inc.) software (Morton et al., 1995, *Anal Biochem;* 227:176-185):

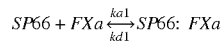

Values were then used to calculate the dissociation constant ($K_D$). Conditions were chosen so that the contribution of mass transport to the observed values of $K_D$ was negligible. Also, models in the T100 evaluation software fit for mass transfer coefficient to mathematically extrapolate the true ka and kd.

FIG. 7 shows visualization of rSV-66 and rSV-170 following separation by SDS-PAGE (left panel) and immunoblotting (right panel). The SDS-PAGE gel was stained with Coomassie Brilliant Blue, while the immunoblot was probed with an anti-His primary antibody and visualized by chemiluminescence. Lanes were loaded with bacterial lysate (L), $Ni^{2+}$ resin purified protein, ($Ni^{2+}$), or protein further purified by RP-HPLC (HPLC). Western blotting of the bacterial lysates was done separately from the Ni2+ and RP-HPLC purified proteins. The figure is therefore a composite, with the lysate lanes aligned with the others based on protein standards, but blotting protocols were identical for all samples.

FIG. 8 shows determination of rSimukunin $IC_{50}$ values for selected serine proteinases. Enzymes, at the concentrations given in Table 1, were incubated with the indicated concentration of rSimukunin for five minutes at 30° C., followed by addition of substrate (250 μM final concentration). The amount of enzyme used in the assays was the lowest possible to give a linear substrate hydrolysis rate in the assays (r2>0.95). Substrate hydrolysis was followed in a Tecan Infinite M200 96-well plate fluorescence reader (Tecan group Ltd, Switzerland) using 365 nm excitation and 450 nm emission wavelength with a cutoff at 435 nm for 20 min at 30° C. Wells without enzyme were used to monitor spontaneous substrate hydrolysis and protease contamination in the inhibitor preparation. All experiments were performed in triplicate (for each enzyme and each concentration of the inhibitor). The mean percentage of enzymatic activity in the presence of various rSimukunin concentrations was then compared with enzymatic activity in the absence of rSimukunin. The sigmoidal fit of the data then yielded the estimate for the $IC_{50}$ of rSimukunin for the various enzymes reported in Table 1.

Example 2

Anti-Inflammatory Effects of Simukunin

The effects of simukunin on inflammatory responses will be studied using various in vitro and in vivo assays. For the in vitro assays, macrophage cell cultures or mouse spleen cell cultures will be exposed to simukunin (or a control treatment, including, but not limited to, saline alone or saline plus an irrelevant protein such as bovine serum albumin (BSA)). Cells will then be challenged with a variety of inflammation-inducing substances including, but not limited to, ATP, endotoxin, and keyhole limpet hemacyanogen (KLH). Murine splenocyte proliferation, including T-cell proliferation, and the secretion of various immune modulators, including, but not limited to, tumor necrosis factor alpha (TNFα), interleukin-2 (IL-2), interferon gamma (IFN-γ), nitric oxide (NO), and superoxide, will be measured. The effect of simukunin on LPS-stimulated B-cell proliferation and mitogen-stimulated mouse splenocyte proliferation, including proliferation of both CD4(+) and CD8(+) T cells, will be determined. The impact of simukunin on the secretion of Th1 cytokines (such as IL-2, IFN-γ, and TGF-β) and Th2 cytokines (such as IL-4, TL-5, IL-6, IL-10, and IL-13) will be determined. The effect of simukunin in both antigen-specific and non-specific immune responses will be assayed. The effect of simukunin on macrophage and dendritic cell viability will be determined. In vivo assays will include the mouse footpad assay. Briefly, mice will be injected in the footpad with either an irritant such as carrageenan, or simukunin plus carrageenan, and inflammation measured by monitoring footpad thickness (a measure of edema and swelling due to cellular infiltration) and myeloperoxidase enzyme activity (a measure of activated neutrophil activity).

Procedures to be followed include, but are not limited to, those described in Wanasen et al., 2004, *Med Vet Entomol;* 18(2):191-9; Wasserman et al., 2004, *Parasite Immunol;* 26(6-7):295-306; Champagne, 2004, *Curr Drug Targets Cardiovasc Haematol Disord;* 4(4):375-96; Champagne, 2005, *Pathophysiol Haemost Thromb;* 34(4-5):221-7; and Tsujimoto et al., 2010, *Parasite Immunol;* 32(4):275-84.

Example 3

Further Characterization of the Effect of Simukunin on Blood Clotting

A rat model of arterial thrombosis may be used to further characterize the effects of simukunin on blood clotting in vivo. Such a rat artery assay may be used to monitor clot formation in response to ADP injection, in the presence and absence of simukunin. Simukunin may be administered intravenously. Procedures to be followed include, for example, those described in more detail by Li et al., 1999, *Arterioscler Thromb Vasc Biol;* 19:378-383; Saldeen et al., 1999, *J Am Coll Cardiol;* 34:1208-1215; Zancan and Mourao, 2004, *Blood Coagul Fibrinolysis;* 15(1): 45-54.

Example 4

Effect of Simukunin on Pathogen Killing by Neutrophils and Macropahges

The effect of simukunin on pathogen killing by neutrophils and macrophages will be determined in various in vitro assays. Neutrophils and macrophages grown in culture will be exposed to various concentrations of simukunin, and their subsequent ability to phagocytose and kill potential pathogens (including, but not limited to, *E. coli, Salmonella*, and *Listeria monocytogenes*) will be measured. Simukunin inhibits cathepsin G and elastase. Both cathepsin G and elastase are involved in pathogen killing as well as phagocytosis. Thus, whether simukunin inhibits the activation and/or the function of innate immune protection against infection will also be investigated. The inhibitory effect of simukunin on elastase and cathepsin G will be determined in various in vivo systems, such as, for example, rat emphysema models (see, for example, Kuraki et al., 2002, *Am J Respir Crit. Care Med;* 166(4):496-500) and mouse models of collagen induced arthritis (see, for example, Raptis et al., 2005, *Immunity;* 22(6):679-691).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be, understood therefrom. The invention is not limited to the exact details shown and described, for variations obvious to one skilled in the art will be included within the invention defined by the claims.

SEQUENCE LISTING FREE TEXT

SEQ ID NO:1 Nucleotide sequence of *Simulium vittatum* SV-66
SEQ ID NO:2 Translated amino acid sequence of *Simulium vittatum* SV-66
SEQ ID NO:3 Amino acid sequence of *Simulium vittatum* SV-66, without 19 amino acid N-terminal signal sequence
SEQ ID NO:4 Nucleotide sequence of *Simulium vittatum* SV-170
SEQ ID NO:5 Translated amino acid sequence of *Simulium vittatum* SV-170
SEQ ID NO:6 Amino acid sequence of *Simulium vittatum* SV-170, without 22 amino acid N-terminal signal sequence
SEQ ID NO:7 Kunitz domain sequence of SV-66
SEQ ID NO:8 Kunitz domain sequence of SV-170
SEQ ID NO:9-11 Kunitz domain sequences of human TFPI
SEQ ID NO:12 Kunitz domain sequences *Bos taurus* BPTI
SEQ ID NO:13-14 Kunitz domain sequences of *Amblyomma hebraeum* Amblin
SEQ ID NO:15-16 Kunitz domain sequences of *Rhipicephalus microplus*: Boophilin
SEQ ID NO:17-36 Synthetic Oligonucleotide Primers

What is claimed is:

1. A method of inhibiting Factor Xa and inhibiting elastase and/or cathepsin G in a subject, the method comprising administering to the subject a composition comprising a polypeptide comprising a Kunitz domain and one or more pharmaceutically acceptable carriers,
wherein the polypeptide comprising a Kunitz domain consists of an isolated simukunin polypeptide comprising an amino acid sequence at least 95% identical to SEQ ID NO:3 or a fragment thereof,
wherein a fragment thereof comprises a Kunitz domain comprising disulfide bonds between cysteine residues C5 to C55, C14 to C38, and C30 to C51 of SEQ ID NO:3 and the reaction site loop (RSL) amino acid residues 12 to 17 of SEQ ID NO:3.

2. The method of claim 1 further inhibiting one or more additional serine proteases.

3. The method of claim 1, further inhibiting Factor IXa, Factor XIa, and/or plasmin.

4. The method of claim 1, further inhibiting kallikrein, trypsin, and/or β-tryptase.

5. The method of claim 1, wherein administration is parenteral.

6. The method of claim 1 wherein plasma coagulation is inhibited.

7. The method of claim 1 inhibiting Factor Xa, elastase and cathepsin G.

8. The method of claim 1, modulating inflammation in the subject.

9. The method of claim 1, modulating the function of neutrophils, macrophages, and/or mast cells in the subject.

10. The method of claim 1, wherein administration is topical.

11. The method of claim 1, wherein the isolated simukunin polypeptide is administered as a sterile, pyrogen-free composition.

12. The method of claim 1, wherein the subject is in need of treatment for a medical condition treated with the administration of an anticoagulant.

13. The method of claim 12, wherein the subject is in need of treatment for a medical treatment to prevent the formation of blood clots and/or the extension of existing blood clots.

14. The method of claim 1, wherein the subject is in need of medical treatment to reduce tissue damage associated with elastase and/or cathepsin G release.

15. The method of claim 14, wherein the subject is in need of treatment for pulmonary emphysema, $\alpha_1$-antitrypsin deficiency, cystic fibrosis, rheumatoid arthritis, keratoconus, asthma, allergies, eczema, and/or cancer.

16. The method of claim 1, wherein the administration of the composition is intravenous, topical, oral, rectal, intranasal, subcutaneous, intraperitoneal, intramuscular, intracardiac, intraosseous, intracerebral, intrathecal, epidural, transdermal, subcutaneous, intracavernous, intravitreal, intraarticular, intrasynovial, transscleral, or intratumor.

17. The method of claim 1, wherein the composition is used to coat a laboratory instrument or device prior to the delivery of the laboratory instrument or device into the subject.

18. A method of inhibiting Factor Xa and inhibiting elastase and/or cathepsin G in a subject, the method comprising administering to the subject a pharmaceutical composition comprising an anti-coagulation factor and one or more pharmaceutically acceptable carriers,
wherein the anti-coagulation factor consists of an isolated simukunin polypeptide comprising an amino acid sequence at least 95% identical to SEQ ID NO:3 or a fragment thereof, and
wherein a fragment thereof comprises a Kunitz domain comprising disulfide bonds between cysteine residues C5 to C55, C14 to C38, and C30 to C51 of SEQ ID NO:3 and the reaction site loop (RSL) amino acid residues 12 to 17 of SEQ ID NO:3.

19. A method of inhibiting Factor Xa and inhibiting elastase and/or cathepsin G in a subject, the method comprising the intravenous administration of an isolated simukunin polypeptide comprising an amino acid sequence at least 95% identical to SEQ ID NO:3 or a fragment thereof to the subject,
wherein a fragment thereof comprises a Kunitz domain comprising disulfide bonds between cysteine residues C5 to C55, C14 to C38, and C30 to C51 of SEQ ID NO:3 and the reaction site loop (RSL) amino acid residues 12 to 17 of SEQ ID NO:3.

20. A method of inhibiting Factor Xa and inhibiting elastase and/or cathepsin G in a subject, the method comprising administering to the subject an isolated simukunin polypeptide comprising an amino acid sequence at least 95% identical to SEQ ID NO:3 or a fragment thereof,
wherein a fragment thereof comprises a Kunitz domain comprising disulfide bonds between cysteine residues C5 to C55, C14 to C38, and C30 to C51 of SEQ ID NO:3 and the reaction site loop (RSL) amino acid residues 12 to 17 of SEQ ID NO:3, and
wherein an isolated simukunin polypeptide comprising an amino acid sequence at least 95% identical to SEQ ID NO:3 or a fragment thereof comprises at least one amino acid alteration from naturally occurring simukunin.

* * * * *